United States Patent
Endl et al.

(10) Patent No.: US 7,807,158 B2
(45) Date of Patent: Oct. 5, 2010

(54) ANTIBODIES AGAINST IL-13 RECEPTOR ALPHA1 AND USES THEREOF

(75) Inventors: Josef Endl, Weilheim (DE); Maria Elena Fuentes, Sunnyvale, CA (US); Yvo Graus, Odijk (NL); Adelbert Grossmann, Eglfing (DE); Sebastian Neumann, Weilheim (DE); Paul Parren, Odijk (NL); Frank Rebers, Utrecht (NL); Joerg Thomas Regula, Munich (DE); Ralf Schumacher, Penzberg (DE); Stefan Seeber, Penzberg (DE); Jan Olaf Stracke, Penzberg (DE); Kay-Gunnar Stubenrauch, Penzberg (DE); Jan Van De Winkel, Zeist (NL); Martine Van Vugt, Houten (NL); Sandra Vereecken-Verploegen, Nieuwegein (NL)

(73) Assignee: Roche Palo Alto LLC, Palo Alto, CA (US)

( * ) Notice: Subject to any disclaimer, the term of this patent is extended or adjusted under 35 U.S.C. 154(b) by 1215 days.

(21) Appl. No.: 11/325,197

(22) Filed: Jan. 3, 2006

(65) Prior Publication Data
US 2006/0263356 A1   Nov. 23, 2006

(30) Foreign Application Priority Data

Jan. 3, 2005  (EP) ................... 05000003
Feb. 3, 2005  (EP) ................... 05002229

(51) Int. Cl.
*A61K 39/395*  (2006.01)
(52) U.S. Cl. ............... 424/133.1; 424/143.1; 530/387.3
(58) Field of Classification Search ........... None
See application file for complete search history.

(56) References Cited

U.S. PATENT DOCUMENTS 5,770,429 A    6/1998  Lonberg et al.
5,859,205 A *  1/1999  Adair et al. ............. 530/387.3

FOREIGN PATENT DOCUMENTS

EP   1 449 851 A1   8/2004
WO   WO 97/15663 A1   5/1997
WO   WO 03/080675 A2   10/2003
WO   WO 2005/019266 A2   3/2005

OTHER PUBLICATIONS

Eduardo Padlan, Mol Immunol. Feb. 1994;31(3):169-217.*
Portolano et al., J Immunol. Feb. 1, 1993;150(3):880-7.*
Vajdos et al., J Mol Biol. Jul. 5, 2002;320(2):415-28.*
Akaiwa, M., et al., "Localization of Human Interleukin 13 Receptor in Non-haematopoietic cells", *Cytokine*, 13, (2001) 75-84.
Brüggemann, M., et al., Designer Mice: The Production of Human Antibody Repertoires in Transgenic Animals, *Year Immunol.*, 7 (1993) 33-40.
Fishwild, D.M. et al., High-avidity human IgGK monoclonal antibodies from a novel strain of minilocus transgenic mice, *Nat. Biotechnol.*, 14 (1996) 845-851.
Graber, P., et al., "The distribution of IL-13 receptor α1 expression on B cells, T cells and monocytes and its regulation by IL-13 and IL-4", *Eur. J. Immunol.*, 28 (1998) 4286-4298.
Jakobovits, A., et al., "Germ-line transmission and expression of a human-derived yeast artificial chromosome", *Nature*, 362 (1993) 255-258.
Jakobovits, A., et al., "Analysis of homozygous mutant chimeric mice: Deletion of the immunoglobulin heavy-chain joining region blocks B-cell development and antibody production", *Proc. Natl. Acad. Sci. USA*, (1993) 2551-2555.
Poudrier, J., et al., "A soluble Form of IL-13 Receptor α1 Promotes IgG2a and IgG2b Production by Murine Germinal Center B Cells", *J. Immunol.*, 163 (1999) 1153-1161.
Poudrier, J. et al., "A novel monoclonal antibody, C41, reveals IL-13Rα1 expression by murine germinal center B cells and follicular dendritic cells", *J. Immunol.*, 30 (2000) 3157-3164.
Van Dijk, .A., et al.,"Human antibodies as next generation therapeutics", *Curr. Opin. Chem. Biol.*, 5 (2001) 368-374.

* cited by examiner

*Primary Examiner*—Zachary Skelding
(74) *Attorney, Agent, or Firm*—Grant D. Green

(57) ABSTRACT

The instant specification discloses an antibody binding to IL-13Rα1, inhibiting IL-13 bioactivity and comprising a variable heavy and a variable light chain, characterized in that the variable heavy chain amino acid sequence CDR3 of this antibody is selected from the group consisting of the heavy chain CDR3 sequences of SEQ ID NO: 1, 3, 5, 7 or 9, and this antibody is useful in the treatment of asthma and allergic diseases.

9 Claims, 3 Drawing Sheets

ANTIBODIES AGAINST IL-13 RECEPTOR ALPHA1 AND USES THEREOF

RELATED APPLICATIONS

This application claims priority from EP05000003.3 filed Jan. 3, 2005 and EP05002229.2 filed Feb. 3, 2005, both incorporated herein by reference in full.

FIELD OF THE INVENTION

This invention relates generally to human antibodies against IL-13 receptor alpha1 (IL-13Rα (alpha)1), methods for their production, and uses.

BACKGROUND OF THE INVENTION

IL-13 is a secreted monomeric peptide produced mainly by Th2 cells but also by mast cells and NK cells. Biological functions of IL-13 include regulation of IgE production and modulation of Th2 development. IL-13 binds to a receptor complex consisting of IL-13 receptor alpha1 (IL-13Rα1) chain and IL-4 receptor alpha (IL-4Rα) chain. IL-13 binding triggers signal transduction events mainly through STAT6. IL-13 binds with low affinity to the IL-13 Rα1 alone and does not bind to IL-4Rα1. Contrary to this, IL-4 binds to IL-4Rα alone and does not bind to IL-13Rα1 alone. Another receptor for IL-13 has been described, the IL-13Rα2. IL-13 binds with high affinity to this receptor. Likely this receptor acts as a decoy receptor.

Inducible overexpression of IL-13 in transgenic mice results in a phenotype that shares many characteristics with asthmatic patients. They show mucus metaplasia, macrophage, lymphocyte and eosinophil-rich inflammation, upregulation of proteases like MMP-9, -12, -13, -2 and -14, cathepsin B, H, K and S and they also present subepithelial fibrosis. Knockout mice for IL-13 show a significant reduction in Th2 cytokine production due to impairment in Th2 development. These mice do not develop airway hyperreactivity (AHR) in spite of the presence of eosinophil inflammation. The AHR was restored by administration of IL-13, indicating that IL-13 is necessary and sufficient for the induction of AHR in mouse. Other important biological functions of IL-13 in relationship with asthma include the induction of goblet cell metaplasia and mucus production. It acts directly on airway epithelial cells, fibroblasts and airway smooth muscle cells and induces different transcriptional programs in each of this cell types. Interestingly, IL-13 decreases the alpha-adrenergic response in smooth muscle cells, contributing to airway narrowing. IL-13 promoter polymorphism is associated with increased risk of allergic asthma. Polymorphisms in the IL-13 gene are associated with high serum IgE levels. Single nucleotide polymorphism in the intergene sequence between the IL-4 and IL-13 genes is associated with atopic asthma.

IL-13 antagonists have been utilized in animal models. For example a soluble mouse IL-13Rα2-IgGFc fusion protein has been used to show efficacy in completely reversing ovalbumin-induced AHR and the number of mucus containing cells. The reversal was obtained even if the treatment is given after full development of the phenotype. In addition, treatment of mice with an IL-13 fusion cytotoxin molecule resulted in reduction of all features of airway disease in a chronic fungal-induced allergic inflammation. In conclusion, IL-13 is a critical mediator of the effector arm of the allergic response.

IL-113Rα1 is a member of the hemapoietin receptor superfamily (type 1 cytokine receptor family) and identified and described by Obiri N. I., et al., *J. Biol. Chem.*, 270 (1995) 8797-8804) and WO 96/29417. It is a protein of 427 amino acids including the signal sequence. Its DNA and protein sequences are described in WO 97/15663 and SwissProt No. P78552. IL-13Rα1 is a glycosylated protein binding to IL-13 with low affinity, but, when linked with IL-4Rα to a heterodimer, it binds IL-13 with high affinity. This complex is also a receptor for IL-4.

Antibodies against IL-13Rα1 are known from WO 96/29417, WO 97/15663, WO 03/080675, Graber P., et al., *Eur. J. Immunol.*, 28 (1998) 4286-4298; Poudrier J., et al., *J. Immunol.*, 163 (1999) 1153-1161; Poudrier J., et al., *Eur. J. Immunol.*, 30 (2000) 3157-3164; Aikawa M., et al., *Cytokine*, 13 (2001) 75-84. Antibodies against IL-13Rα1 are commercially available from R&D Systems Inc. USA.

SUMMARY OF THE INVENTION

The invention comprises an antibody binding to IL-13Rα1 and inhibiting IL-13 bioactivity, characterized in that the variable heavy chain amino acid sequence CDR3 of said antibody is selected from the group consisting of the heavy chain CDR3 sequences of SEQ ID NO: 1, 3, 5, 7 or 9.

The antibody is preferably a human antibody.

The antibody is preferably characterized by an affinity of $10^{-9}$ M ($K_D$) or less, preferably of $10^{-9}$ to $10^{-13}$ M for binding to IL-13Rα1.

Preferably the antibody is characterized in that its heavy chain CDR1, CDR2 and CDR3 sequences are selected from the group consisting of the heavy chain CDR1, CDR2 and CDR3 sequences of SEQ ID NO: 1, 3, 5, 7 or 9.

The antibody is preferably characterized in that the variable light chain amino acid sequences CDR1, CDR2 and CDR3 of said antibody are selected from the group consisting of the light chain CDR sequences of SEQ ID NO: 2, 4, 6, 8 or 10.

The antibody is preferably characterized in that the variable heavy chain amino acid sequences CDR1, CDR2 and CDR3 of said antibody are selected from the group consisting of the heavy chain CDR sequences of SEQ ID NO: 1, 3, 5, 7 or 9 and the variable light chain amino acid sequences CDR1, CDR2 and CDR3, of said antibody are selected from the group consisting of the light chain CDR sequences of SEQ ID NO: 2, 4, 6, 8 or 10.

The CDR sequences are preferably selected independently of each other and are separated by FR (framework) regions.

The antibody is preferably characterized in comprising as heavy chain CDRs the CDRs of SEQ ID NO: 1 and as light chain CDRs the CDRs of SEQ ID NO: 2, as heavy chain CDRs the CDRs of SEQ ID NO: 3 and as light chain CDRs the CDRs of SEQ ID NO: 4, as heavy chain CDRs the CDRs of SEQ ID NO: 5 and as light chain CDRs the CDRs of SEQ ID NO: 6, as heavy chain CDRs the CDRs of SEQ ID NO: 7 and as light chain CDRs the CDRs of SEQ ID NO: 8 or as heavy chain CDRs the CDRs of SEQ ID NO: 9 and as light chain CDRs the CDRs of SEQ ID NO: 10.

The CDR sequences can be determined according to the standard definition of Kabat et al., Sequences of Proteins of Immunological Interest, 5th ed., Public Health Service, National Institutes of Health, Bethesda, Md. (1991). On this basis, the complementarity determining regions (CDRs) of SEQ ID NO: 1-8 have the following sequences:

Heavy chain CDRs: CDR1 (aa 31-35) of SEQ ID NO: 1, 3, 5, 7, 9, CDR2 (aa 50-66) of SEQ ID NO: 1, 3, 5, 7, 9, CDR3 (aa 99-108) of SEQ ID NO: 1, 3, 9, CDR3 (aa 99-107) of SEQ ID NO: 5, CDR3 (aa 99-112) of SEQ ID NO: 7;

Light chain CDRs: CDR1 (aa 24-34) of SEQ ID NO: 2, 4, 6, 10, CDR1 (aa 24-35) of SEQ ID NO: 8, CDR2 (aa 50-56)

of SEQ ID NO: 2, 4, 6, 10, CDR2 (aa 51-57) of SEQ ID NO:8 and CDR3 (aa 89-97) of SEQ ID NO: 2, 4, 6, 10, CDR3 (aa 90-97) of SEQ ID NO: 8.

Preferably, the invention provides an antibody comprising as complementarity determining regions (CDRs) the following sequences:
a) an antibody heavy chain comprising heavy chain CDRs of SEQ ID NO:1, 3, 5, 7 or 9;
b) an antibody light chain comprising light chain CDRs of SEQ ID NO:2, 4, 6, 8 or 10, wherein the CDRs are selected independently of each other.

The antibody is preferably characterized in comprising as heavy chain variable region SEQ ID NO: 1 and as light chain variable region SEQ ID NO: 2, as heavy chain variable region SEQ ID NO: 3 and as light chain variable region of SEQ ID NO: 4, as heavy chain variable region SEQ ID NO: 5 and as light chain variable region SEQ ID NO: 6, as heavy chain variable region SEQ ID NO: 7 and as light chain variable region SEQ ID NO: 8 or as heavy variable region SEQ ID NO: 9 and as light chain variable region SEQ ID NO: 10.

The antibody is preferably characterized in comprising
  a) as heavy chain variable region SEQ ID NO: 1, as light chain variable region SEQ ID NO: 2, as κ light chain constant region SEQ ID NO: 11 and as γ1 heavy chain constant region SEQ ID NO: 12 optionally with mutations L234A and L235A or D265A and N297A,
  b) as heavy chain variable region SEQ ID NO: 3 and as light chain variable region of SEQ ID NO: 4, as κ light chain constant region SEQ ID NO: 11 and as γ1 heavy chain constant region SEQ ID NO: 12 optionally with mutations L234A and L235A or D265A and N297A,
  c) as heavy chain variable region SEQ ID NO: 5 and as light chain variable region SEQ ID NO: 6, as κ light chain constant region SEQ ID NO: 11 and as γ1 heavy chain constant region SEQ ID NO: 12 optionally with mutations L234A and L235A or D265A and N297A,
  d) as heavy chain variable region SEQ ID NO: 7 and as light chain variable region SEQ ID NO: 8, as κ light chain constant region SEQ ID NO: 11 and as γ1 heavy chain constant region SEQ ID NO: 12 optionally with mutations L234A and L235A or D265A and N297A, or
  e) as heavy variable region SEQ ID NO: 9 and as light chain variable region SEQ ID NO: 10, as κ light chain constant region SEQ ID NO: 11 and as γ1 heavy chain constant region SEQ ID NO: 12 optionally with mutations L234A and L235A or D265A and N297A.

Preferably the antibody is characterized in binding to IL-13Rα1 in competition to antibody LC5002-002, LC5002-003, LC5002-005, LC5002-007 and/or LC5002-018.

Preferably the antibody is characterized in comprising as variable regions the variable regions of LC5002-002, LC5002-003, LC5002-005, LC5002-007 or LC5002-018. The variable regions of these antibodies are shown in SEQ ID NO: 1-10. Useful constant regions are well known in the state of the art. Examples are shown in SEQ ID NO: 11-12.

The antibody is preferably a monoclonal or a recombinantly produced antibody.

In one embodiment of the invention the antibody is a class-altered human antibody.

In a preferred embodiment of the invention the antibody contains a human γ1 heavy chain comprising
a) amino acid sequence $Pro_{233}Val_{234}Ala_{235}$ with deletion of $Gly_{236}$ and/or amino acid sequence $Gly_{327}Leu_{328}Pro_{329}Ser_{330}Ser_{331}$ SEQ ID NO:13,
b) amino acid sequence $Ala_{234}Ala_{235}$ or
c) amino acids $Ala_{265}$ and $Ala_{297}$.

Preferably the antibody according to the invention inhibits IL-13 induced Stat-6 phosphorylation with an $IC_{50}$ value of 6 nM or lower, inhibits IL-13 induced eotaxin production with an $IC_{50}$ value of 20 nM or lower and/or inhibits IL-13 or IL-4 induced cell proliferation, preferably of TF-1 cells (ATCC CRL 2003) with an $IC_{50}$ value of 10 nM or lower (IL-13) and 60 nM or lower (IL-4). IL-13 induced Stat-6 phosphorylation, eotaxin production and induction of cell proliferation are determined according to examples 6 to 8.

The antibody according to the invention preferably does not bind to denatured IL-13Rα1 ($K_D$ for binding affinity $10^{-6}$ M or higher). The antibody is preferably characterized by showing substantially no crossreactivity with IL-13Rα2 and IL-4Rα ($K_D$ for binding affinity $10^{-6}$ M or higher).

The invention further provides hybridoma cell lines which produce antagonistic monoclonal antibodies against IL-13Rα1.

The preferred hybridoma cell lines according to the invention (hu-MAB<h-IL-13R alpha>LC.5002-002 (DSM ACC2709), hu-MAB<h-IL-13Ralpha>LC.5002-003 (DSM ACC2710), hu-MAB<h-IL-13Ralpha>LC.5002-005 (DSM ACC2711), hu-MAB<h-IL-13R alpha>LC.5002-007 (DSM ACC2712)) were deposited 13.01.2005 with Deutsche Sammlung von Mikroorganismen und Zellkulturen GmbH (DSMZ), Germany.

The antibodies obtainable from said cell lines are embodiments of the invention.

The invention further provides nucleic acids encoding polypeptides of which antibodies according to the invention are comprised, expression vectors comprising said nucleic acids, and host cells for the recombinant production of such antibodies. The invention further provides methods for the recombinant production of such antibodies.

The polypeptides encoded by the nucleic acids according to the invention are
a) an antibody heavy chain comprising heavy chain CDRs of SEQ ID NO: NO: 1, 3, 5, 7 or 9 and
b) an antibody light chain comprising light chain CDRs of SEQ ID NO: 2, 4, 6, 8 or 10.

These polypeptides are capable of assembling together with the respective other antibody chain to generate an antibody.

Antibodies according to the invention show benefits for patients in need of corticosteroid therapy. The antibodies according to the invention have new and inventive properties causing a benefit for a patient suffering from asthma or an allergic disease.

The invention further provides methods for treating asthma and allergic diseases.

The invention further comprises the use of an antibody according to the invention for asthma treatment and for the manufacture of a pharmaceutical composition according to the invention. In addition, the invention comprises a method for the manufacture of a pharmaceutical composition according to the invention.

The invention further comprises a pharmaceutical composition comprising an antibody according to the invention with a pharmaceutically effective amount, optionally together with a buffer and/or an adjuvant useful for the formulation of antibodies for pharmaceutical purposes.

The invention further provides pharmaceutical compositions comprising such antibodies in a pharmaceutically acceptable carrier. In one embodiment, the pharmaceutical composition may be included in an article of manufacture or kit.

The invention further comprises a vector comprising a nucleic acid according to the invention, capable of expressing said nucleic acid in a prokaryotic or eukaryotic host cell.

The invention further comprises a prokaryotic or eukaryotic host cell comprising a vector according to the invention.

The invention further comprises a method for the production of a recombinant human antibody according to the invention, characterized by expressing a nucleic acid according to the invention in a prokaryotic or eukaryotic host cell and recovering said antibody from said cell. The invention further comprises the antibody obtainable by such a recombinant method.

The invention further comprises a method for the preparation of a pharmaceutical composition characterized in selecting an antibody against IL-13Rα1 from a plurality of antibodies against IL-13Rα1 when compared to such an assay without said antibody, producing said antibody by means of recombinant expression, recovering said antibody and combining said antibody with a pharmaceutical acceptable buffer and/or adjuvant. Preferably the antibody has one or more of the above mentioned additional properties.

DETAILED DESCRIPTION OF THE INVENTION

The terms "IL-13Rα1, murine IL-13Rα1, IL-13, IL-13Rα2 and IL-4Rα" and their domains are well known in the state of the art and e.g. defined by SwissProt P78552, O09030, P35225, Q14627 and P24394. If not otherwise stated, the terms "IL-13Rα1, IL-13, IL-13Rα2 and IL-4Rα" therefore denotes the human polypeptides IL-13Rα1, IL-13, IL-13Rα2 and IL-4Rα.

The term "human antibody", as used herein, includes antibodies having variable and constant regions (domains) which can be assigned to defined human germ line immunoglobulin sequences because of their high sequence similarity or identity with these germ line sequences. Human antibodies are well-known in the state of the art (van Dijk, M. A., and van de Winkel, J. G., Curr. Opin. Chem. Biol. 5 (2001) 368-374). Human antibodies can also be produced in transgenic animals (e.g. mice) that are capable, upon immunization, of producing a full repertoire or a selection of human antibodies in the absence of endogenous immunoglobulin production. Transfer of the human germ-line immunoglobulin gene array in such germ-line mutant mice results in the production of human antibodies upon antigen challenge (see, e.g., Jakobovits, A., et al., Proc. Natl. Acad. Sci. USA 90 (1993) 2551-2555; Jakobovits, A., et al., Nature 362 (1993) 255-258; Bruggemann, M., et al., Year Immunol. 7 (1993) 33-40). Human antibodies can also be produced in phage display libraries (Hoogenboom, H. R., and Winter, G., J. Mol. Biol. 227 (1992) 381-388; Marks, J. D., et al., J. Mol. Biol. 222 (1991) 581-597). The techniques of Cole et al. and Boemer et al. are also available for the preparation of human monoclonal antibodies (Cole et al., Monoclonal Antibodies and Cancer Therapy, Alan R. Liss, p. 77 (1985); and Boerner, P., et al., J. Immunol. 147 (1991) 86-95). A human antibody encompasses the various forms of antibodies, preferably monoclonal antibodies including but not being limited to whole antibodies, antibody fragments, class-altered antibodies and genetically engineered antibodies (variant or mutant antibodies) as long as the characteristic properties according to the invention are retained. Especially preferred are recombinant human antibodies. The term "monoclonal antibody" as used herein refers to a preparation of antibody molecules all having substantially the same amino acid sequence.

The term "recombinant human antibody", as used herein, is intended to include all human antibodies that are prepared, expressed, created or isolated by recombinant means, such as antibodies isolated from a host cell such as a NSO or CHO cell or from an animal (e.g. a mouse) that is transgenic for human immunoglobulin genes or antibodies expressed using a recombinant expression vector transfected into such a host cell. Such recombinant human antibodies have variable and constant regions in a rearranged form. The recombinant human antibodies according to the invention have been subjected to in vivo somatic hypermutation. Thus, the amino acid sequences of the VH and VL regions of the recombinant antibodies are sequences that can be assigned to defined human germ line VH and VL sequences, but may not naturally exist within the human antibody germ line repertoire in vivo.

The term "class-altered antibody" refers to a monoclonal antibody, preferably a human antibody, comprising a variable region, i.e., binding region, from one source or germ line and at least a portion of a constant region that matches a constant region of an antibody from a different source or germ line, usually prepared by recombinant DNA techniques. Such class-altered antibodies are not naturally occurring and therefore not available directly from xenograft mice. Forms of "class-altered antibodies" encompassed by the present invention are those in which the constant region has differences from the wild-type constant region sequence that result in an antibody having different properties according to the invention, especially in regard to C1q binding and/or Fc receptor (FcR) binding, i.e. by change or mutation of Fc. Class-altered antibodies are the product of expressed immunoglobulin genes comprising DNA segments encoding immunoglobulin variable regions and DNA segments encoding immunoglobulin constant regions. Methods for producing class-altered antibodies involve conventional recombinant DNA and gene transfection techniques are well known in the art (see, e.g., Morrison, S. L., et al., Proc. Natl. Acad. Sci. USA 81 (1984) 6851-6855; U.S. Pat. Nos. 5,202,238 and 5,204,244).

The "variable region" (variable region of a light chain (VL), variable region of a heavy chain (VH)) as used herein denotes the part of each of the pair of light and heavy chains which is involved directly in binding the antibody to the antigen. The domains of variable human light and heavy chains have the same general structure and each domain comprises four framework (FR) regions whose sequences are widely conserved, connected by three "hypervariable regions" (or complementarity determining regions, CDRs). The framework regions adopt a β(beta)-sheet conformation and the CDRs may form loops connecting the β-sheet structure. The CDRs in each chain are held in their three-dimensional structure by the framework regions and form together with the CDRs from the other chain the antigen binding site. The antibody heavy and light chain CDR3 regions, preferably the heavy chain CDR3, play a particularly important role in the binding specificity/affinity of the antibodies according to the invention and therefore provide a further object of the invention.

The terms "hypervariable region" or "antigen-binding portion of an antibody" when used herein refer to the amino acid residues of an antibody which are responsible for antigen-binding. The hypervariable region comprises amino acid residues from the "complementarity determining regions" or "CDRs". "Framework" or "FR" regions are those variable domain regions other than the hypervariable region residues as herein defined. Therefore, the light and heavy chains of an antibody comprise from N- to C-terminus the domains FR1, CDR1, FR2, CDR2, FR3, CDR3, and FR4. CDR and FR regions are determined according to the standard definition of Kabat et al., Sequences of Proteins of Immunological Interest, 5th ed., Public Health Service, National Institutes of Health, Bethesda, Md. (1991).

The "constant domains" are not involved directly in binding of an antibody to an antigen, but exhibit various effector functions. Depending on the amino acid sequence of the constant region of their heavy chains, antibodies or immunoglobulins are divided into the classes: IgA, IgD, IgE, IgG and IgM, and several of these may be further divided into subclasses (isotypes), e.g. IgG1, IgG2, IgG3, and IgG4, IgA1 and IgA2. The heavy chain constant regions that correspond to the different classes of immunoglobulins are called μ, δ, γ, α, and ε, respectively. The antibodies according to the invention are preferably of IgG1 type.

The Fc part of an antibody is directly involved in complement activation, C1q binding, C3 activation and Fc receptor binding. Binding to C1q is caused by defined binding sites in the Fc part. Such binding sites are known in the state of the art and described e.g. by Lukas, T. J., et al., *J. Immunol.* 127 (1981) 2555-2560; Brunhouse, R., and Cebra, J. J., *Mol. Immunol.* 16 (1979) 907-917; Burton, D. R., et al., *Nature* 288 (1980) 338-344; Thommesen, J. E., et al., *Mol. Immunol.* 37 (2000) 995-1004; Idusogie, E. E., et al., *J. Immunol.* 164 (2000) 4178-4184; Hezareh, M., et al., *J. Virol.* 75 (2001) 12161-12168; Morgan, A., et al., *Immunology* 86 (1995) 319-324; and EP 0 307 434. Such binding sites are e.g. L234, L235, D270, N297, E318, K320, K322, P331 and P329 (numbering according to EU index of Kabat, see below). Antibodies of subclass Ig1, IgG2 and IgG3 usually show complement activation, C1q binding and C3 activation, whereas IgG4 antibodies do not activate the complement system, do not bind C1q and do not activate C3. As used herein the term "Fc part derived from human origin" denotes a Fc part which preferably has an amino acid sequence of a Fc part of a human antibody of the subclass IgG1 modified in such a way that no C1q binding, C3 activation and/or FcR binding can be detected or binding is at least reduced for 50%, preferably 70%, compared to a human IgG1 antibody. An "Fc part of an antibody" is a term well known to the skilled artisan and defined on the basis of papain cleavage of antibodies. The antibodies according to the invention contain as Fc part, preferably with an amino acid sequence of a Fc part derived from human origin and preferably all other parts of the human constant regions. Preferably the Fc part is a mutated human Fc part from human IgG1 subclass. Mostly preferred are Fc parts comprising a γ1-heavy chain constant region (an example is shown in SEQ ID NO: 11) with mutations L234A and L235A or D265A and N297A (WO99/51642).

Human constant chains, e.g. γ1-heavy chains are described in detail by Kabat et al., Sequences of Proteins of Immunological Interest, 5th Ed. Public Health Service, National Institutes of Health, Bethesda, Md. (1991), and by Bruggemann, M., et al., J. Exp. Med. 166 (1987) 1351-1361; Love, T. W., et al., Methods Enzymol. 178 (1989) 515-527. The constant domains preferred in the invention provide no complement binding. The "variable region" (variable region of a light chain (VL), variable region of a heavy chain (VH)) as used herein denotes each of the pair of light and heavy chains which is involved directly in binding the antibody to the antigen.

The term nucleic acid or nucleic acid molecule, as used herein, is intended to include DNA molecules and RNA molecules. A nucleic acid molecule may be single-stranded or double-stranded, but preferably is double-stranded DNA.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are cis, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included. Where distinct designations are intended, it will be clear from the context.

The term "binding to IL-13Rα1" as used herein means the binding of the antibody to IL-13Rα1 in an in vitro assay, preferably in a binding assay in which the antibody is bound to a surface and binding of IL-13Rα1 is measured by Surface Plasmon Resonance (SPR). Binding means a binding affinity ($K_D$) of $10^{-8}$ M or less, preferably $10^{-13}$ to $10^{-9}$ M. "No binding" means a $K_D$ of $10^{-6}$ M or more. The antibodies according to the invention bind to the extracellular domain of human IL-13Rα1 and preferably also of mouse IL-13Rα1.

Binding to IL-13Rα1 can be investigated by a BIAcore assay (Pharmacia Biosensor AB, Uppsala, Sweden). The affinity of the binding is defined by the terms ka (rate constant for the association of the antibody from the antibody/antigen complex), kd (dissociation rate), and $K_D$ (kd/ka).

The binding of IL-13 to IL-13Rα1 is inhibited by the antibodies according to the invention. The inhibition is measured as $IC_{50}$ in an ELISA for binding of IL-13 to IL-13Rα1/IL-4Rα heterodimer. For performing such an assay IL-13Rα1 is immobilized and IL-13 and IL-4Rα are added. The $IC_{50}$ values of the antibodies according to the invention for the binding of IL-13 to IL-13Rα1 are no more than 6 nM. $IC_{50}$ values are measured as average or median values of at least three independent measurements. Single $IC_{50}$ values may be out of the scope.

The antibodies according to the invention show preferably a binding to the same epitopes of IL-13Rα1 as an antibody selected from the group consisting of antibodies LC5002-002, LC5002-003, LC5002-005, LC5002-007 or LC5002-018 or are inhibited in binding to IL-13Rα1 due to steric hindrance of binding by these antibodies. Binding inhibition can be detected by an SPR assay using an immobilized antibody selected from the group consisting of antibodies LC5002-002, LC5002-003, LC5002-005, LC5002-007 or LC5002-018 and IL-13Rα1 at a concentration of 20-50 nM and the antibody to be detected at a concentration of 100 nM. A signal reduction of 50% or more shows that the antibody competes with an antibody selected from the group consisting of antibodies LC5002-002, LC5002-003, LC5002-005, LC5002-007 or LC5002-018. The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics.

Conformational and nonconformational epitopes are distinguished in that the binding to the former but not the latter is lost in the presence of denaturing solvents. The invention comprises also a human antibody binding to IL-13Rα1 and inhibiting IL-13 bioactivity, characterized by an affinity of $10^{-9}$ M ($K_D$) or less, preferably of $10^{-9}$ to $10^{-13}$ M for binding to IL-13Rα1 and by an affinity of $10^{-7}$ M ($K_D$) or less, preferably of $10^{-8}$ to $10^{-9}$ M for binding to murine IL-13Rα1.

In a preferred embodiment of the invention, the antibodies according to the invention are further characterized by one or more of the characteristics selected from the group selected from the binding parameters ka, kd and $K_D$, binding to the same epitope to which an antibody selected from the group consisting of antibodies LC5002-002, LC5002-003, LC5002-005, LC5002-007 or LC5002-018 binds.

The antibodies according to the invention are preferably produced by recombinant means. Such methods are widely known in the state of the art and comprise protein expression in prokaryotic and eukaryotic cells with subsequent isolation of the antibody polypeptide and usually purification to a pharmaceutically acceptable purity. For the protein expression, nucleic acids encoding light and heavy chains or fragments thereof are inserted into expression vectors by standard methods. Expression is performed in appropriate prokaryotic or eukaryotic host cells like CHO cells, NS0 cells, SP2/0 cells, HEK293 cells, COS cells, yeast, or *E. coli* cells, and the antibody is recovered from the cells (supernatant or cells after lysis).

Recombinant production of antibodies is well-known in the state of the art and described, for example, in the review articles of Makrides, S. C., *Protein Expr. Purif.* 17 (1999) 183-202; Geisse, S., et al., *Protein Expr. Purif.* 8 (1996) 271-282; Kaufman, R. J., *Mol. Biotechnol.* 16 (2000) 151-161; Werner, R. G., *Drug Res.* 48 (1998) 870-880.

The antibodies may be present in whole cells, in a cell lysate, or in a partially purified or substantially pure form. Purification is performed in order to eliminate other cellular components or other contaminants, e.g. other cellular nucleic acids or proteins, by standard techniques, including alkaline/SDS treatment, CsCl banding, column chromatography, agarose gel electrophoresis, and others well known in the art. See Ausubel, F., et al., ed. Current Protocols in Molecular Biology, Greene Publishing and Wiley Interscience, New York (1987).

Expression in NS0 cells is described by, e.g., Barnes, L. M., et al., *Cytotechnology* 32 (2000) 109-123; and Barnes, L. M., et al., *Biotech. Bioeng.* 73 (2001) 261-270. Transient expression is described by, e.g., Durocher, Y., et al., *Nucl. Acids. Res.* 30 (2002) E9. Cloning of variable domains is described by Orlandi, R., et al., *Proc. Natl. Acad. Sci. USA* 86 (1989) 3833-3837; Carter, P., et al., *Proc. Natl. Acad. Sci. USA* 89 (1992) 4285-4289; and Norderhaug, L., et al., *J. Immunol. Methods* 204 (1997) 77-87. A preferred transient expression system (HEK 293) is described by Schlaeger, E.-J., and Christensen, K., in *Cytotechnology* 30 (1999) 71-83 and by Schlaeger, E.-J., in *J. Immunol. Methods* 194 (1996) 191-199.

The control sequences that are suitable for prokaryotes, for example, include a promoter, optionally an operator sequence, and a ribosome binding site. Eukaryotic cells are known to utilize promoters, enhancers and polyadenylation signals.

The monoclonal antibodies are suitably separated from the culture medium by conventional immunoglobulin purification procedures such as, for example, protein A-Sepharose, hydroxylapatite chromatography, gel electrophoresis, dialysis, or affinity chromatography. DNA and RNA encoding the monoclonal antibodies is readily isolated and sequenced using conventional procedures. The hybridoma cells can serve as a source of such DNA and RNA. Once isolated, the DNA may be inserted into expression vectors, which are then transfected into host cells such as CHO cells, HEK 293 cells, or myeloma cells that do not otherwise produce immunoglobulin protein, to obtain the synthesis of recombinant monoclonal antibodies in the host cells.

The antibodies according to the invention include, in addition, such antibodies having "conservative sequence modifications", nucleotide and amino acid sequence modifications which do not affect or alter the above-mentioned characteristics of the antibody according to the invention. Modifications can be introduced by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g. glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in a human anti-IL-13Rα1 antibody can be preferably replaced with another amino acid residue from the same side chain family.

Amino acid substitutions can be performed by mutagenesis based upon molecular modeling as described by Riechmann, L., et al., *Nature* 332 (1988) 323-327 and Queen, C., et al., *Proc. Natl. Acad. Sci. USA* 86 (1989)10029-10033.

Amino acid sequence variants of human IL-13Rα1 antibody are prepared by introducing appropriate nucleotide changes into the antibody DNA, or by peptide synthesis. Such modifications can be performed, however, only in a very limited range, e.g. as described above. For example, the modifications do not alter the abovementioned antibody characteristics such as the IgG isotype and epitope binding, but may improve the yield of the recombinant production, protein stability or facilitate the purification.

Any cysteine residue not involved in maintaining the proper conformation of the anti-IL-13Rα1 antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

Another type of amino acid variant of the antibody alters the original glycosylation pattern of the antibody. By altering is meant deleting one or more carbohydrate moieties found in the antibody, and/or adding one or more glycosylation sites that are not present in the antibody. Glycosylation of antibodies is typically N-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. Addition of glycosylation sites to the antibody is conveniently accomplished by altering the amino acid sequence such that it contains one or more of the above-described tripeptide sequences (for N-linked glycosylation sites).

Nucleic acid molecules encoding amino acid sequence variants of anti-IL-13Rα1 antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of anti-IL-13Rα1 antibody.

Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330, and in Aplin, J. D., and Wriston, J. C. Jr., *CRC Crit. Rev. Biochem.* (1981) 259-306.

Removal of any carbohydrate moieties present on the antibody may be accomplished chemically or enzymatically. Chemical deglycosylation can be accomplished by exposing the antibody to trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Sojahr, H. T., and Bahl, O. P., *Arch. Biochem. Biophys.* 259 (1987) 52-57 and by Edge, A. S., et al. *Anal. Biochem.* 118 (1981) 131-137. Enzymatic cleavage of carbohydrate moieties on antibodies can be achieved by the use of a variety of endo- and exo-glycosidases as described by Thotakura, N. R., and Bahl, O. P., *Meth. Enzymol.* 138 (1987) 350-359.

Another type of covalent modification of the antibody comprises linking the antibody to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

In yet another aspect, the invention provides isolated B-cells from a transgenic non-human animal, e.g. a transgenic mouse, which express the human anti-IL-13Rα1 antibodies according to the invention. Preferably, the isolated B cells are obtained from a transgenic non-human animal, e.g., a transgenic mouse, which has been immunized with a purified or enriched preparation of IL-13Rα1 antigen and/or cells expressing IL-13Rα1. Preferably, the transgenic non-human animal, e.g. a transgenic mouse, has a genome comprising a human heavy chain transgene and a human light chain transgene encoding all or a portion of an antibody of the invention. The isolated B-cells are then immortalized to provide a source (e.g. a hybridoma) of human anti-IL-13Rα1 antibodies. Accordingly, the present invention also provides a hybridoma capable of producing human monoclonal antibodies according to the invention. In one embodiment, the hybridoma includes a B cell obtained from a transgenic non-human animal, e.g., a transgenic mouse having a genome comprising a human heavy chain transgene and a human light chain transgene encoding all or a portion of an antibody of the invention, fused to an immortalized cell.

In a particular embodiment, the transgenic non-human animal is a transgenic mouse having a genome comprising a human heavy chain transgene and a human light chain transgene encoding all or a portion of an antibody of the invention. The transgenic non-human animal can be immunized with a purified or enriched preparation of IL-13Rα1 antigen and/or cells expressing IL-13Rα1. Preferably, the transgenic non-human animal, e.g. the transgenic mouse, is capable of producing IgG1 isotypes of human monoclonal antibodies to IL-13Rα1.

The human monoclonal antibodies according to the invention can be produced by immunizing a transgenic non-human animal, e.g. a transgenic mouse, having a genome comprising a human heavy chain transgene and a human light chain transgene encoding all or a portion of an antibody of the invention, with a purified or enriched preparation of IL-13Rα1 antigen and/or cells expressing IL-13Rα1. B cells (e.g. splenic B cells) of the animal are then obtained and fused with myeloma cells to form immortal, hybridoma cells that secrete human monoclonal antibodies against IL-13Rα1.

In a preferred embodiment, human monoclonal antibodies directed against IL-13Rα1 can be generated using transgenic mice carrying parts of the human immune system rather than the mouse system. These transgenic mice, referred to herein as "HuMab" mice, contain a human immunoglobulin gene miniloci that encodes unrearranged human immunoglobulin genes which include the heavy (μ and γ) and κ light chain (constant region genes), together with targeted mutations that inactivate the endogenous μ and κ chain loci (Lonberg, N., et al., *Nature* 368 (1994) 856-859). Accordingly, the mice exhibit reduced expression of mouse IgM or K, and in response to immunization, the introduced human heavy and light chain transgenes undergo class switching and somatic mutation to generate high affinity human IgG monoclonal antibodies (Lonberg, N., et al., *Nature* 368 (1994) 856-859; reviewed in Lonberg, N., *Handbook of Experimental Pharmacology* 113 (1994) 49-101; Lonberg, N., and Huszar, D., *Intern. Rev. Immunol.* 25 (1995) 65-93; and Harding, F., and Lonberg, N., *Ann. N. Acad. Sci* 764 (1995) 536-546). The preparation of HuMab mice is described in Taylor, L., et al., *Nucleic Acids Res* 20 (1992) 6287-6295; Chen, J., et al., *Int'l Immunol* 5 (1993) 647-656; Tuaillon, N., et al., *Proc. Natl. Acad. Sci USA* 90 (1993) 3720-3724; Choi, T. K., et al., *Nature Genetics* 4 (1993) 117-123; Chen, J., et al., *EMBO J.* 12 (1993) 821-830; Tuaillon, N., et al., *Immunol.* 152 (1994) 2912-2920; Lonberg, N., et al., *Nature* 368 (1994) 856-859; Lonberg, N., *Handbook of Experimental Pharmacology* 113 (1994) 49-101; Taylor, L., et al., *Int. Immunol.* 6 (1994) 579-591; Lonberg, N., and Huszar, D., *Intern. Rev. Immunol.* 25 (1995) 65-93; Harding, F., and Lonberg, N., *Ann. N. Acad. Sci* 764 (1995) 536-546; Fishwild, D. M., et al., *Nat. Biotechnol.* 14 (1996) 845-851, the contents of all of which are hereby incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; 5,545,807; 5,770,429; WO 98/24884; WO 94/25585; WO 93/1227; WO 92/22645; and WO 92/03918.

To generate fully human monoclonal antibodies to IL-13Rα1, HuMab mice can be immunized with a purified or enriched preparation of IL-13Rα1 antigen and/or cells expressing IL-13Rα1 in accordance with the general method, as described by Lonberg, N., et al., *Nature* 368 (1994) 856-859; Fishwild, D. M., et al., *Nat. Biotechnol.* 14 (1996) 845-851 and WO 98/24884. Preferably, the mice will be 6-16 weeks of age upon the first immunization. For example, a purified or enriched preparation of soluble IL-13Rα1 antigen (e.g. purified from IL-13Rα1-expressing cells) can be used to immunize the HuMab mice intraperitoneally. In the event that immunizations using a purified or enriched preparation of IL-13Rα1 antigen do not result in antibodies, mice can also be immunized with cells expressing IL-13Rα1, e.g., a tumor cell line, to promote immune responses. Cumulative experience with various antigens has shown that the HuMab transgenic mice respond best when initially immunized intraperitoneally (i.p.) with antigen in complete Freund's adjuvant, followed by every other week alternatingly i.p. or s.c. immunizations (for example, up to a total of 6) with antigen in incomplete Freund's adjuvant. The immune response can be monitored over the course of the immunization protocol with plasma samples being obtained by retroorbital bleeds. The plasma can be screened by ELISA, and mice with sufficient titers of anti-IL-13Rα1 human immunoglobulin can be used for immortalization of corresponding B cells. Mice can be boosted intravenously with antigen 3 to 4 days before sacrifice and removal of the spleen and lymph nodes. It is expected that 2-3 fusions for each antigen may need to be performed. Several mice will be immunized for each antigen. For example, a total of five to twelve HuMab mice of the HCo7 and HCo12 strains can be immunized.

The HCo7 mice have a JKD disruption in their endogenous light chain (kappa) genes (as described in Chen, J., et al., *EMBO J.* 12 (1993) 821-830), a CMD disruption in their endogenous heavy chain genes (as described in Example 1 of WO 01/14424), a KCo5 human kappa light chain transgene (as described in Fishwild, D. M., et al., *Nat. Biotechnol.* 14 (1996) 845-851), and a HCo7 human heavy chain transgene (as described in U.S. Pat. No. 5,770,429).

The HCo 12 mice have a JKD disruption in their endogenous light chain (kappa) genes (as described in Chen, J., et al., *EMBO J.* 12 (1993) 821-830), a CMD disruption in their endogenous heavy chain genes (as described in Example 1 of WO 01/14424), a KCo5 human kappa light chain transgene (as described in Fishwild, D. M., et al., *Nat. Biotechnol.* 14 (1996) 845-851), and a HCo12 human heavy chain transgene (as described in Example 2 of WO 01/14424).

The mouse lymphocytes can be isolated and fused with a mouse myeloma cell line using PEG based on standard protocols to generate hybridomas. The resulting hybridomas are then screened for the production of antigen-specific antibodies. For example, single cell suspensions of splenic and lymph node-derived lymphocytes from immunized mice are fused to one-sixth the number of SP 2/0 nonsecreting mouse myeloma cells (ATCC, CRL 1581) with 50% PEG. Cells are plated at approximately $2 \times 10^5$ in flat bottom microtiter plate, followed by about two weeks incubation in selective medium.

Individual wells are then screened by ELISA for human anti-IL-13Rα1 monoclonal IgM and IgG antibodies. Once extensive hybridoma growth occurs, medium is analyzed, usually after 10-14 days. The antibody secreting hybridomas are replated, screened again, and if still positive for human IgG, anti-IL-13Rα1 monoclonal antibodies, can be subcloned at least twice by limiting dilution. The stable subclones are then cultured in vitro to produce antibody in tissue culture medium for characterization.

Because CDR sequences are responsible for antibody-antigen interactions, it is possible to express recombinant antibodies according to the invention by constructing expression vectors that include the CDR sequences according to the invention onto framework sequences from a different human antibody (see, e.g., Riechmann, L., et al., *Nature* 332 (1998) 323-327; Jones, P., et al., *Nature* 321 (1986) 522-525; and Queen, C., et al., *Proc. Natl. Acad. See. USA* 86 (1989)10029-10033). Such framework sequences can be obtained from public DNA databases that include germline human antibody gene sequences. These germline sequences will differ from mature antibody gene sequences because they will not include completely assembled variable genes, which are formed by V(D)J joining during B cell maturation. Germline gene sequences will also differ from the sequences of a high affinity secondary repertoire antibody at individual evenly across the variable region.

The invention preferably comprises a nucleic acid fragment encoding a polypeptide binding to IL-13Rα1, whereby said polypeptide inhibits the binding of IL-13 to IL-13Rα1, selected from the group consisting of
a) an antibody heavy chain comprising heavy chain CDRs of SEQ ID NO: 1, 3, 5, 7 or 9;
b) an antibody light chain comprising light chain CDRs of SEQ ID NO: 2, 4, 6, 8 or 10.

The reconstructed heavy and light chain variable regions are combined with sequences of promoter, translation initiation, constant region, 3' untranslated, polyadenylation, and transcription termination to form expression vector constructs. The heavy and light chain expression constructs can be combined into a single vector, co-transfected, serially transfected, or separately transfected into host cells which are then fused to form a single host cell expressing both chains.

Accordingly, the invention provides a method for the production of a recombinant human antibody according to the invention, comprising expressing a nucleic acid encoding
a) an antibody heavy chain comprising heavy chain CDRs of SEQ ID NO: 1, 3, 5, 7 or 9;
b) an antibody light chain comprising light chain CDRs of SEQ ID NO: 2, 4, 6, 8 or 10.

The invention further comprises the use of an antibody according to the invention for the detection of IL-13Rα1 in vitro, preferably by an immunological assay determining the binding between IL-13Rα1 of a sample and the antibody according to the invention.

In another aspect, the present invention provides a composition, e.g. a pharmaceutical composition, comprising one or a combination of human monoclonal antibodies, or the antigen-binding portion thereof, of the present invention, formulated together with a pharmaceutically acceptable carrier.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g. by injection or infusion).

A "pharmaceutically acceptable salt" refers to a salt that retains the desired biological activity of the antibody and does not impart any undesired toxicological effects (see e.g. Berge, S. M., et al., *J. Pharm. Sci.* 66 (1977) 1-19). Such salts are included in the invention. Examples of such salts include acid addition salts and base addition salts. Acid addition salts include those derived from nontoxic inorganic acids, such as hydrochloric salts.

A composition of the present invention can be administered by a variety of methods known in the art. As will be appreciated by the skilled artisan, the route and/or mode of administration will vary depending upon the desired results.

To administer a compound of the invention by certain routes of administration, it may be necessary to coat the compound with, or coadminister the compound with, a material to prevent its inactivation. For example, the compound may be administered to a subject in an appropriate carrier, for example, liposomes, or a diluent. Pharmaceutically acceptable diluents include saline and aqueous buffer solutions.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The composition must be sterile and fluid to the extent that the composition is deliverable by syringe. In addition to water, the carrier can be an isotonic buffered saline solution, ethanol, polyol (for example, glycerol, propylene glycol, and liquid polyetheylene glycol, and the like), and suitable mixtures thereof.

Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

The following examples, references, sequence listing and figures are provided to aid the understanding of the present invention, the true scope of which is set forth in the appended claims. It is understood that modifications can be made in the procedures set forth without departing from the spirit of the invention.

DESCRIPTION OF THE SEQUENCE LISTING

SEQ ID NO:1 heavy chain variable domain of HuMab LC5002-002
SEQ ID NO:2 light chain variable domain of HuMab LC5002-002
SEQ ID NO:3 heavy chain variable domain of HuMab LC5002-003
SEQ ID NO:4 light chain variable domain of HuMab LC5002-003
SEQ ID NO:5 heavy chain variable domain of HuMab LC5002-005
SEQ ID NO:6 light chain variable domain of HuMab LC5002-005
SEQ ID NO:7 heavy chain variable domain of HuMab LC5002-007
SEQ ID NO:8 light chain variable domain of HuMab LC5002-007
SEQ ID NO:9 heavy chain variable domain of HuMab LC5002-018
SEQ ID NO:10 light chain variable domain of HuMab LC5002-018
SEQ ID NO:11 κ light chain constant region
SEQ ID NO:12 γ1 heavy chain constant region
SEQ ID NO:13 First variation in heavy chain
SEQ ID NO:14 Site varied in heavy chain
SEQ ID NO:15 Site of second variation in heavy chain

EXAMPLES

Example 1

Generation of Hybridomas

Figure 1:
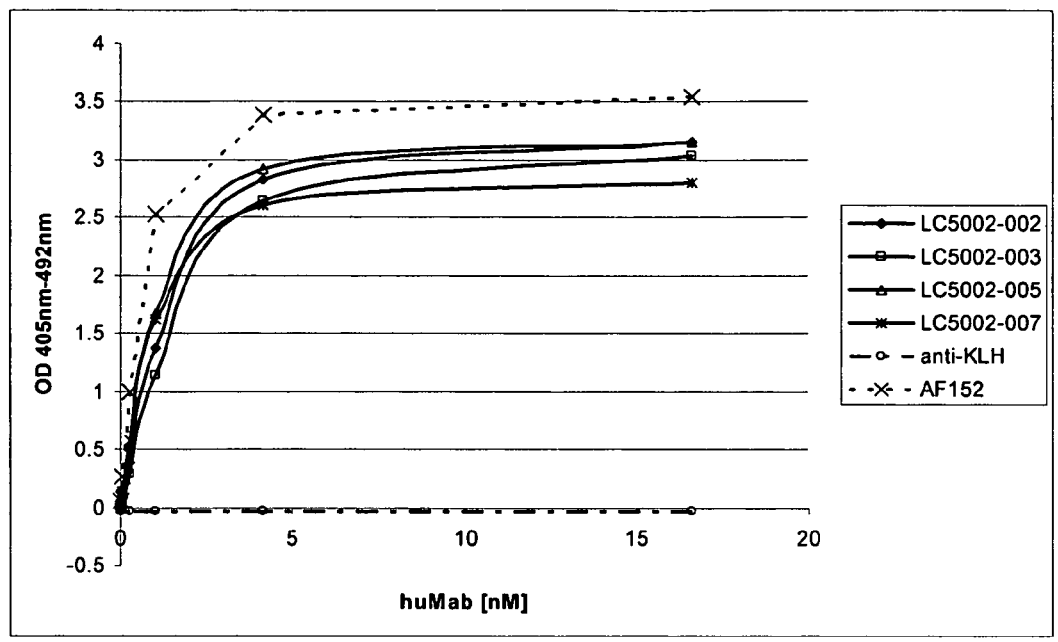
FIG. 1 shows binding of anti-IL-13Rα1 antibodies to immobilized recombinant human IL-13Rα1 polypeptide. Included are polyclonal rabbit-anti-human IL-13Rα1 antibody AF152 (R&D systems) and anti-KLH as a negative control HuMab.

The human monoclonal antibodies according to the invention can be produced by immunizing a transgenic non-human animal, e.g. a transgenic mouse having a genome comprising a human heavy chain transgene and a human light chain transgene encoding all or a portion of an antibody of the invention, with cells expressing human IL-13Rα1. B cells (e.g. splenic B cells) of the animal are then obtained and fused with myeloma cells to form immortal, hybridoma cells that secrete human monoclonal antibodies against IL-13Rα1. Human monoclonal antibodies directed against human IL-13Rα1 can be generated using transgenic mice carrying parts of the human immune system rather than the mouse system. These transgenic mice, referred to herein as "HuMab" mice, contain a human immunoglobulin gene minilocus that encodes unrearranged human immunoglobulin genes which include the heavy (μ and γ) and κ (kappa) light chain (constant region genes), together with targeted mutations that inactivate the endogenous μ and kappa chain loci (Lonberg N., et al., *Nature* 368 (1994) 856-859). Accordingly, the mice exhibit reduced expression of mouse IgM or K, and in response to immunization, the introduced human heavy and light chain transgenes undergo class switching and somatic mutation to generate high affinity human IgG monoclonal antibodies. To generate fully human monoclonal antibodies to human IL-13Rα1, HuMab mice can be immunized with cells expressing human IL-13Rα1 in accordance with the general method, as described by Lonberg, N., et al., *Nature* 368 (1994) 856-859; Fishwild, D. M., et al., *Nat. Biotechnol.* 14 (1996) 845-851 and WO 98/24884. Preferably, the mice will be 6-16 weeks of age upon the first immunization. For example, IL-13Rα1 transfected cells can be used to immunize the HuMab mice intraperitoneally. The immune response can be monitored over the course of the immunization protocol with plasma samples being obtained by retroorbital bleeds. The plasma can be screened by ELISA and/or FACS. Mice with sufficient titers of anti-human IL-13Rα1 human immunoglobulin can be used for immortalization of corresponding B cells. Mice can be boosted intravenously with antigen 3 to 4 days before sacrifice and removal of the spleen and lymph nodes. For example, HuMab mice of the HCo7 or HCo12 strain can be immunized. The HCo7 mice have a JKD disruption in their endogenous light chain (kappa) genes (as described in Chen et al. (1993) *EMBO J.* 12: 821-830), a CMD disruption in their endogenous heavy chain genes (as described in Example 1 of WO 01/14424), a KCo5 human kappa light chain transgene (as described in Fishwild, D. M., et al. (1996) *Nature Biotechnol* 14:845-851), and a HCo7 human heavy chain transgene (as described in U.S. Pat. No. 5,770,429). The HCo12 mice have a JKD disruption in their endogenous light chain (kappa) genes (as described in Chen, J., et al., *EMBO J.* 12 (1993) 821-830), a CMD disruption in their endogenous heavy chain genes (as described in Example 1 of WO 01/14424)) a KCo5 human kappa light chain transgene (as described in Fishwild, D. M., et al., *Nat. Biotechnol.* 14 (1996) 845-851, and a HCo12 human heavy chain transgene (as described in Example 2 of WO 01/14424). The mouse lymphocytes can be isolated and fused with a mouse myeloma cell line using PEG based on standard protocols to generate hybridomas. The resulting hybridomas are then screened for the production of antigen-specific antibodies. For example, single cell suspensions of splenic and lymph node derived lymphocytes from immunized mice are fused to SP 2/0 nonsecreting mouse myeloma cells (ATCC, CRL 1581) with 50% PEG. Cells are plated at approximately $0.75 \times 10^7$ in flat bottom micro titer plate, followed by about two weeks incubation in selective medium.

Individual wells are then screened by ELISA and/or FACS for human anti-IL-13Rα1 monoclonal IgM and IgG antibodies. Once extensive hybridoma growth occurs, the antibody secreting hybridomas are replated, screened again, and if still positive for human IgG, anti-IL-13Rα1 monoclonal antibodies, can be subcloned at least twice by limiting dilution. The stable subclones are then cultured in vitro to produce antibody in tissue culture medium for characterization.

Immunization procedure of transgenic mice: Three HCo7 mice (3 males), strain GG2201 (Medarex, San Jose, Calif., USA) and 2 HCo12 mice (1 male and 1 female), strain GG2198 (Medarex, San Jose, Calif., USA) were immunized with $1 \times 10^6$ HEK293 cells, transfected with an expression vector for IL-13Rα1. In total eight immunizations were given alternating intraperitoneally (i.p.) and subcutaneous (s.c.) at the tail base. For the first immunization, 100 μl of $1 \times 10^6$ HEK293: IL-13Rα1 cells, was mixed with 100 μl complete Freund's adjuvant (CFA; Difco Laboratories, Detroit, USA). For all other immunizations, 100 μl of cells in PBS was mixed with 100 μl incomplete Freund's adjuvant (ICFA; Difco).

Boosting of mice: When serum titers of anti-IL-13Rα1 were found to be sufficient, mice were additionally boosted twice with $1 \times 10^6$ HEK293: IL-13Rα1 cells in 200 μl PBS intravenously (i.v.) 4 and 3 days before fusion.

Example 2

Testing the Binding of HuMab to Immobilized IL-13Rα1 by ELISA

To determine the ability of the antibodies of the invention to bind to recombinant IL-13Rα1, the extracellular domain of IL-13Rα1 (R&D Systems, UK) was dissolved in PBS (1 μg/ml) and allowed to adsorb to microtiter plates (NUNC Maxisorb) by incubation over night at 4° C. After washing the plates with washing buffer (WB=0.9% NaCl; 0.1% Tween® 20) unspecific binding sites were blocked by addition of 100 μl incubation buffer (IB=PBS with 1% crotein C and 0.1% Tween® 20) and incubation for 30 min at room-temperature (RT). Then, serially diluted HuMab and control antibodies (100 μl/well; dilutions in IB) were added and incubated for 1 hour at RT. The plates were again washed, and bound human antibodies were detected by incubation with peroxidase-conjugated rabbit anti-human kappa (DAKO, Denmark) in a final dilution of 1:500 in IB. Polyclonal goat anti-hIL-13Rα1 antibodies were detected with peroxidase-conjugated polyclonal donkey anti-goat IgG (Santa Cruz; dilution 1:1000 in IB). After incubation for 1 h at RT and a subsequent washing step, the plates were developed with ready-to-use ABTS® solution (Roche Diagnostics GmbH) at RT in the dark. Absorbance was measured at 405 nm after absorbance of the highest concentration reached a sufficient OD.

All antibodies against IL-13Ralpha1 tested were able to bind to immobilized extracelluar domains of human IL-13Rα1. The EC50 values determined were in the range of 0.5-2 nM for the various LC antibodies tested. The negative control HuMab anti-KLH did not bind to the immobilized extracellular domains of IL-13Rα1. Polyclonal goat-anti human IL-13Rα1 antibody, included as positive control, also bound efficiently to the immobilized extracellular domains of IL-13Rα1 (FIG. 1).

Example 3

Inhibition of IL-13 Binding to IL-13Rα1/IL-4Rα Heterodimer (ELISA)

Microtiter plates were coated with 100 μl hIL-13Rα1:hFc chimeric protein (R&D Systems, UK) in PBS at 3 μg/ml at 4° C. overnight on a shaker. After washing the plates with WB, serially diluted HuMab and control antibodies (100 μl/well; dilutions in IB) were added and incubated for 30 min at RT. The plates were again washed, and then a mixture of IL-13

(R&D Systems, UK; 0.5 µg/ml; dilution with IB) and IL-4Rα (R&D Systems, UK; 0.75 µg/ml; dilution with IB) were added and incubated for 1 h at RT. After washing the plates 100 µl biotinylated anti IL-13 antibody (BAF213; R&D Systems, UK) in a concentration of 0.4 µg/ml was added and incubated for 1 h at RT. After washing the plates, bound IL-13 was detected by peroxidase-coupled streptavidin (Roche Diagnostics GmbH, DE) in a dilution of 1:5000 in IB (incubation period 1 h at RT). Finally, plates were washed and developed with ready-to-use ABTS® solution (Roche Diagnostics GmbH, DE) at room temperature (RT) in the dark. Absorbance was measured at 405 nm after 45 to 60 minutes.

Figure 2:
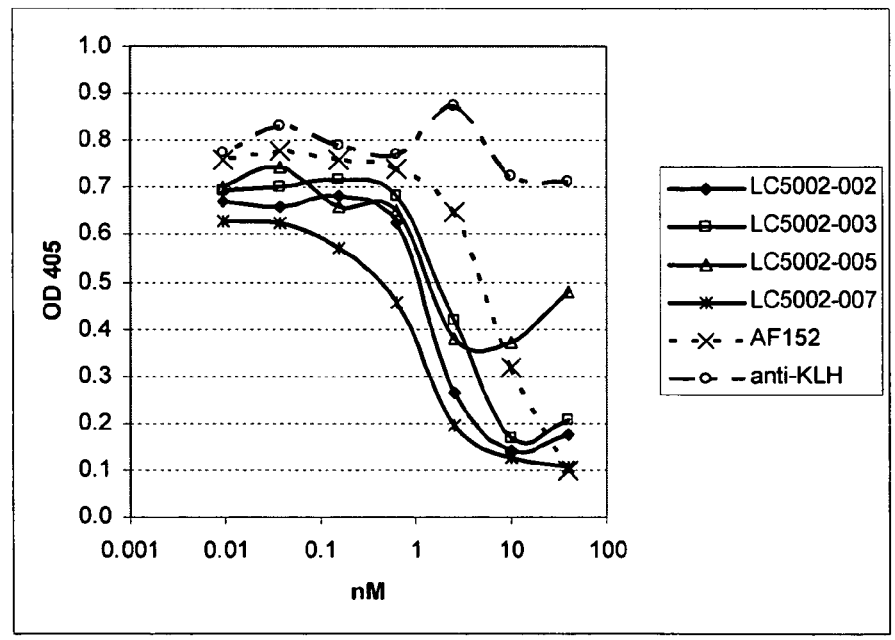
FIG. 2 shows inhibition of IL-13 binding to immobilized IL-13Rα1/IL-4Rα receptor by anti-IL-13Rα1 antibodies.

Antibodies LC5002-002, LC5002-003, LC5002-005, LC5002-007 and LC5002-018 were able to inhibit binding of IL-13 to the heterodimeric receptor with maximal inhibition values ranging from approximately 50% to 80-85%. Positive control was AF152 (polyclonal rabbit antibody). As expected, the negative control anti-KLH did not inhibit binding of IL-13 to the heterodimeric receptor. The $IC_{50}$ values obtained were between 1.5 nM and 10.1 nM for LC5002-002, LC5002-003, LC5002-005, LC5002-007 and LC5002-018 (FIG. 2).

Example 4

Radioligand Binding Assay $^{125}$I-IL-13 binding assay was performed using CHO cells expressing human IL-13Rα1 and human IL-4Rα in binding buffer (25 mM HEPES, 150 mM NaCl, 1 mM $CaCl_2$, 5 mM $MgCl_2$, and 0.5% bovine serum albumin, adjusted to pH 7.2). $1 \times 10^5$ cells per well were mixed with the antibodies and preincubated for 15 minutes to 1 hour. 0.1 nM $^{125}$I-IL-13 was added, and the mix was incubated at 4° C. for 4 hours. The concentration of $^{125}$I-IL-13 used in the assay was determined from saturation binding analysis, competition analysis and determination of input $^{125}$I-IL-13 to reach equilibrium binding with the cell line. Samples were harvested onto a GF/C filter plate pretreated with 1% PEI/0.5% BSA and counted on Packard TopCount Scintillation counter. Data analysis was performed in PRISM using nonlinear regression curve fit (GraphPad Software, San Diego, Calif.).

Figure 3:
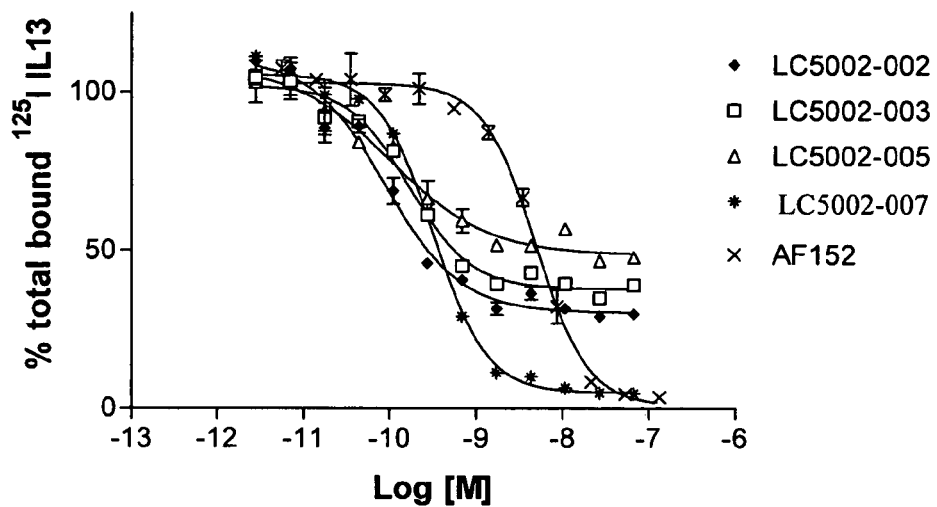
FIG. 3 shows the blockade of IL-13 binding to CHO cells (expressing IL-13Ralpha1 and IL-4Rα2) by anti-IL-13Rα1 antibodies. As a positive control, a commercially available polyclonal anti-IL-13Rα1 antibody (AF152, R&D Systems, Minneapolis, Minn.) was included.

All antibodies aganist IL-13Ralpha1 tested block binding of labeled IL-13 to the IL-13Rα1/IL-4Rα complex. The calculated $IC_{50}$ values for antibodies LC5002-002, LC5002-003, LC5002-005, LC5002-007 and LC5002-018 were between 0.09 nM and 0.32 nM and 84.8 nM for AF152 (FIG. 3).

Example 5

Inhibition of IL-13 Induced Upregulation of CD23 on Human B Cells and Monocytes by HuMab Peripheral blood mononuclear cells (PBMC) were isolated by a Ficoll Hypaque density gradient. After washing the cells with RPMI they were resuspended in RPMI/10% FCS and distributed at $3 \times 10^5$ PBMC/well (volume 50 µl) in 96 well flat bottom microtiter plates (Corning Incorporated Costar). Then, 25 µl of an anti-human CD40 antibody (Immunotech) in a final concentration 0.5 µg/ml in RPMI/10% FCS and 25 µl of an anti-human IgA+IgG+IgM antibody (Immunoresearch) in a final concentration of 10 µg/ml in RPMI/10% FCS were added. Then serially diluted HuMab and control antibodies (50 µl/well; dilutions in RPMI/10% FCS) were added and the cells incubated for 30 min in the incubator (37° C.; 5% $CO_2$). Then recombinant human IL-13 (R&D Systems) in a final concentration of 0.67 ng/ml was added (50 µl/well) and the cells incubated for 72 h at 37° C./5% $CO_2$. After this incubation the plates were centrifuged and the medium aspirated. For detachment of adherent cells 200 µl of Accutase (PAA) was added and the cells incubated for approximately 5 min at 37° C.; 5% $CO_2$. The cells were detached by repeated flushing and transferred to a round bottom plate. After centrifugation and aspiration of the supernatants the cells were incubated with 200 µl of a mixture of anti-CD23-PE, anti-CD20-FITC and anti-CD14-APC (all from BD Biosciences Pharmingen, San Diego, Calif.). The cells were incubated for 30 min at 4° C., then centrifuged and the supernatants aspirated. This washing step was repeated once, and finally the cells were resuspended in 200 µl of PBS/0.1% human serum albumin and analysed in a FACS Calibur flow cytometer (BD Biosciences Pharmingen, San Diego, Calif.) using the CellQuest software. In most cases, 10000 events were acquired and gated on a light scatter gate to include only viable lymphocytes and monocytes. The cells were pregated on a CD19 positive cluster for B lymphocytes or a CD14 positive cluster for monocytes and analyzed further for CD23 expression.

The observed $IC_{50}$ values for inhibiting of CD23 upregulation on B-lymphocytes were between 0.5 nM and >70 nM for antibodies LC5002-002, LC5002-003, LC5002-005, LC5002-007 and LC5002-018, and 13.6 nM for AF152. A similar profile was found for inhibition of IL-13 induced CD23 upregulation on human monocytes. On monocytes the $IC_{50}$ values were between 0.1 nM and 62.8 nM for antibodies LC5002-002, LC5002-003, LC5002-005, LC5002-007 and LC5002-018, and 62.9 nM for AF152.

Example 6

TF-1 Proliferation Assay in Response to IL-13 or IL-4 Asstimulus

TF-1 cells (ATCC # CRL 2003) were grown in media containing ATCC modified RPMI, 10% FBS, 1× Pencillin/Streptomycin, 2 ng/ml GM-CSF. A day prior to the assay the cells were maintained in GM-CSF free media. $5 \times 10^3$ cells per well were incubated with appropriate concentrations of anti-IL-13Rα1 antibodies at 37° C. for 1 hour. Then the cells were stimulated with 2 ng/ml of human IL-13 (R&D Systems, Minneapolis, Minn.) or 0.1 ng/ml of human IL-4 (R&D Systems, Minneapolis, Minn.) and incubated at 37° C. for 48 hours. The cells were pulsed with 0.5 µCi $^3$H-Thymidine and incubated at 37° C. for 16-18 hours. Samples were harvested onto GFC plates pretreated with 1% PEI/0.25% BSA using Perkin Elmer Filtermate 96 harvester. The GFC plates were counted on a Perkin Elmer Top count Scintillation counter. Data analysis was performed in PRISM using nonlinear regression curve fit (GraphPad Software, San Diego, Calif.).

Anti-KLH antibody did not show any inhibition in this assay. The same was true for LC5002-007. All other antibodies inhibited the response, even though LC5002-007 inhibited the response with higher IC value than the other antibodies. The observed $IC_{50}$ values for the different antibodies were: 13.50 nM for AF152, 9.21 nM for LC5002-002, 3.07 nM for LC5002-003 and 0.39 nM for LC5002-005. A similar profile was found for IL-4-induced TF-1 cell proliferation, however the potency of the antibodies was decreased compared to IL-13-induced responses. $IC_{50}$ values for IL-4-induced proliferation were 0.02 nM for anti-IL-4R antibody, 74.37 mM for AF152 and for antibodies LC5002-002, LC5002-003, LC5002-005, LC5002-007 and LC5002-018 between 4.68 nM and 60 nM.

Example 7

Inhibition of Eotaxin Production in Response to IL-13 by Human Lung Fibroblast

The assay was performed using HFL-1 cells (Human Lung Fibroblast, ATCC # CCL-153). Cells were plated at a density of 100,000 cells per well in a 12-well plate and incubated at 37° C. for 72 hours to reach confluency. Cells were then starved in serum free medium for 24 h and treated with anti-IL-13Rα1 antibody at 37° C. for 1 h. Following this treatment cells were stimulated with 10 ng/ml IL-13 (R&D Systems, Minneapolis, Minn.) at 37° C. for 48 h. Supernatants were collected and eotaxin determinations were done using commercially available ELISA from R&D Systems (Cat. No. DTX00). Absorbance was read using Spectromax microplate reader and the data was analyzed using PRISM (GraphPad Software, San Diego, Calif.).

The antibodies tested showed different capability to inhibit eotaxin release. With the exeption of LC5002-007 all other antibodies tested showed some inhibition. The calculated average $IC_{50}$ values from 3 to 4 different experiments were 11.5 nM for AF152 and between 2.45 nM and 19.8 nM for antibodies LC5002-002, LC5002-003, LC5002-005, LC5002-007 and LC5002-018.

Example 8

Inhibition of IL-13-Induced Stat-6 Phosphorylation in Human Bronchial Smooth Muscle Cells Human Bronchial Smooth Muscle Cells (BSMC; Clonetics, Cat. No CC-2576) were grown following the manufacturer's instructions. Cells were grown in 12-well tissue culture plates until they reached confluency. Cells were starved for 24 h in serum-free medium and variable amounts of antibody were added. Plates were incubated for 1 h and then stimulated with 2.5 ng/ml IL-13 (R&D System). After 15 min incubation, supernatant was removed, cells were washed with phosphate buffer and 100 µl of lysis buffer was added. The mix was briefly sonicated on ice and centrifuged. Lysate was used for Western Blot detection of phophorylated Stat-6. Equal amounts of protein were loaded onto an SDS-gel, run and transferred to a membrane. Anti-Stat-6 antibody was from Santa Cruz Biotechnology (Cat. No. SC-11762R) and a secondary antibody coupled to peroxidase was used. Detection was done using the ECL Plus System from Amersham (Cat No RPN 2132). Quantitation was done in a Typhoon 9400 Imager.

Both HuMabs tested in this assay (LC50002-003 and LC5002-005) inhibited IL-13-induced Stat-6 phosphorylation. The potency found in this assay was similar to that of other functional assays. The calculated $IC_{50}$ values were 18.64 nM for AF152, 5.98 nM for LC5002-003 and 1.18 nM for LC5002-005.

Example 9

Cloning and Sequence Analysis of Anti-hIL-13Rα1 HuMab Variable Domains (K-Light and γ1-Heavy Chains)

The nucleotide sequences coding for the light chain variable region $V_L$ and the heavy chain variable region $V_H$ of the anti hIL-13Rα1 HuMabs were isolated by a standard cDNA synthesis/PCR procedure. Total RNA was prepared from $1\times10^6$-$1\times10^7$ hybridoma cells using the GeneRacer™ Kit (Invitrogen). Hybridoma derived RNA was used as a template for the $1^{st}$ strand cDNA synthesis and ligation of the GeneRacer™ Oligo-dT Primer. $2^{nd}$-strand cDNA synthesis and further PCR amplification of $V_L$ and $V_H$ encoding cDNA fragments were performed with reverse light and heavy chain primers complementary to nucleotide sequences of the κ-light and γ1-heavy chain constant region and 5'-specific GeneRacer™ primers, respectively. The PCR products were cloned using the TOPO™ TA cloning kit from Invitrogen™ Life Technologies and pCR4-TOPO™ as a cloning vector. Cloned PCR products were identified by restriction mapping of the appropriate plasmids using EcoRI for digestion and expected/calculated DNA fragment sizes of about 740 and 790 bp for $V_L$ and $V_H$, respectively. The DNA sequence of cloned PCR fragments was determined by double strand sequencing. The GCG (Genetics Computer Group, Madison, Wis.) software package version 10.2 and Vector-NTI 8 (InforMax, Inc) was used for general data processing. DNA and protein sequences were aligned using the GCG modul CLUSTALW. Sequence alignments were made using the program GENEDOC (version 2.1).

Example 10

Construction of Expression Plasmids for an Anti-hIL-13Rα1 IgG1 HuMab

The anti-hIL-13Rα1 HuMab light and heavy chain encoding genes were separately assembled in mammalian cell expression vectors. Thereby the gene segments encoding the anti-hIL-13Rα1 HuMab light chain variable region ($V_L$) and the human κ-light chain constant region (CL, SEQ ID NO: 11) were joined as were gene segments for the anti-hIL-13Rα1 HuMab heavy chain variable region ($V_H$) and the human γ1-heavy chain constant region ($C_{H1}$-Hinge-$C_{H2}$—$C_{H3}$, SEQ ID NO: 12). General information regarding the nucleotide sequences of human light and heavy chains from which the codon usage is given in: Kabat, E. A., Wu, T. T., Perry, H. M., Gottesman, K. S., and Foeller, C., (1991) Sequences of Proteins of Immunological Interest, Fifth Ed., NIH Publication No. 91-3242. The transcription unit of the anti-hIL-13Rα1 HuMab κ-light chain is composed of the following elements:

The immediate early enhancer and promoter from the human cytomegalovirus (HCMV), A synthetic 5'-UT including a Kozak sequence, A murine immunoglobulin heavy chain signal sequence including the signal sequence intron, The cloned anti-hIL-13Rα1 HuMab variable light chain cDNA arranged with a unique BsmI restriction site at the 5' end and a splice donor site and a unique NotI restriction site at the 3' end, The genomic human K-gene constant region, including the intron 2 mouse Ig-K enhancer [Picard, D., and Schaffner, W., Nature 307 (1984) 80-82] and The human immunoglobulin K-polyadenylation ("poly A") signal sequence.

The transcription unit of the anti-hIL-13Rα1 HuMab γ1-heavy chain is composed of the following elements:

The immediate early enhancer and promoter from the human cytomegalovirus (HCMV), A synthetic 5'-UT including a Kozak sequence, A modified murine immunoglobulin heavy chain signal sequence including the signal sequence intron, The cloned anti-hIL-13Rα1 HuMab variable heavy chain cDNA arranged with a unique BsmI restriction site at the 5' and a splice donor site and a unique NotI restriction site at the 3' end, The genomic human γ1-heavy gene constant region, including the mouse Ig μ-enhancer (Neuberger, M. S., EMBO J. 2 (1983) 1373-1378), The human γ1-immunoglobulin polyadenylation ("poly A") signal sequence.

Functional elements of the anti-hIL-13Rα1 HuMab κ-light chain and γ1-heavy chain expression plasmids:

Besides the anti-hIL-13Rα1 HuMab κ-light chain or γ1-heavy chain expression cassette these plasmids contain A hygromycin resistance gene An origin of replication, oriP, of Epstein-Barr virus (EBV)

An origin of replication from the vector pUC 18 which allows replication of this plasmid in E. coli, and A β-lactamase gene which confers ampicillin resistance in E. coli.

Example 11

Construction of Expression Plasmids for Mutant (Variant) Anti-hIL-13Rα1 IgG1

Expression plasmids encoding mutant anti-hIL-13Rα1 γ1-heavy chains can be created by site-directed mutagenesis of the wild type expression plasmids using the Quick-Change™ Site-Directed mutagenesis Kit (Stratagene) and are desribed in table 1. Amino acids are numbered according to EU numbering (Edelman, G. M., et al., Proc. Natl. Acad. Sci. USA 63 (1969) 78-85; Kabat, E. A., Wu, T. T., Perry, H. M., Gottesman, K. S., and Foeller, C., (1991) Sequences of Proteins of Immunological Interest, Fifth Ed., NIH Publication No. 91-3242).

TABLE 1

| Mutation | Description |
| --- | --- |
| PVA-236; GLPSS331 as specified by E233P; L234V; L235A; delta G236; | The amino acid sequence $Glu_{233}Leu_{234}Leu_{235}Gly_{236}$ (SEQ ID NO: 14) of the human γ1-heavy chain is replacedby the amino acid sequence $Pro_{233}Val_{234}Ala_{235}$ of the human γ2-heavy chain. |
| A327G; A330S; P331S | The amino acid sequence $Ala_{327}Leu_{328}Pro_{329}Ala_{330}Pro_{331}$ (SEQ ID NO: 15) of the human γ1-heavy chain is replaced by the amino acid sequence $Gly_{327}Leu_{328}Pro_{329}Ser_{330}Ser_{331}$ (SEQ ID NO: 13) of the human γ 4-heavy chain |
| L234A; L235A | The amino acid sequence $Leu_{234}Leu_{235}$ of the human γ1 -heavy chain is replaced |

TABLE 1-continued

| Mutation | Description |
| --- | --- |
| | by the amino acid sequence $Ala_{234}Ala_{235}$ |

Example 12

Production of Recombinant Anti-hIL-13Rα1 HuMabs

Recombinant HuMabs were generated by transient transfection of adherent HEK293-EBNA cells (ATTC CRL-10852) cultivated in DMEM (Gibco) supplemented with 10% ultra-low IgG FCS (Gibco), 2 mM Glutamine (Gibco), 1% v/v nonessential aminoacids (Gibco) and 250 μg/ml G418 (Roche Diagnostics GmbH, DE). For transfection Fugene™ 6 (Roche Diagnostics GmbH, DE) transfection reagent was used in a ratio of reagent (μl) to DNA (μg) ranging from 3:1 to 6:1. Immunoglobulin light and heavy chains were expressed from two different plasmids using a molar ratio of light chain to heavy chain encoding plasmid from 1:2 to 2:1. HuMab containing cell culture supernatants were harvested at day 4 to 11 after transfection.

General information regarding the recombinant expression of human antibody in e.g. HEK293 is given in: Meissner, P., et al., Biotechnol Bioeng 75 (2001) 197-203.

Example 13 a) Affinity Analysis of HuMabs LC5002-003, -005, and -007 Using Chimeric hIL-13Rα1:hFc For interaction analysis a Biacore 3000 instrument was used. As running and reaction buffer, HBS-P (10 mM HEPES, 150 mM NaCl, 0.005% polysurfactant P, pH 7.4) at 25° C. was used. Capturing molecules (goat anti-human-IgG, Fcγ specifc) were amine-coupled at a concentration of 20 μg/ml at a flow rate of 5 μl/min for 20 minutes. HuMabs were injected at a concentration of 1 μg/ml at a flow rate of 10 μl/min for 1 minute. Blocking of the free goat anti human IgG, Fcγ was achieved by injecting human gamma globulin at 500 nM and 30 μl/min for 3 minutes. Analyte (hIL-13Rα1:hFc chimeric protein) was injected for two minutes at five concentrations between 5.63 nM and 90 nM and washed with HBS-P for five minutes. Regeneration of the surface was accomplished by two injections of 100 mM HCl for 1 min each. The chip, assay format and sequence of injections and kinetic data correspond to the description in table 2. Negative control data (e.g. buffer curves) were subtracted from sample curves for correction of system intrinsic baseline drift and for noise signal reduction. BiaEvaluation version 4.01 was used for analysis of sensorgrams and for calculation of affinity data. Kinetic data were calculated by fitting kinetic data to a 1:1 Langmuir binding model (Table 2).

TABLE 2

Affinity analysis of HuMabs using hIL-13Rα1:hFc.
Data analysis based on 1:1 Langmuir binding model.

| Chip | Capturing | Ligand | Analyte | $k_a$ (1/Ms) | $k_d$ (1/s) | $K_D$ (M) |
| --- | --- | --- | --- | --- | --- | --- |
| CM5 | Anti-hFcγ | LC5002-003 | hIL-13Rα1:hFc | $2.1 \times 10^5$ | $1.4 \times 10^{-6}$ | $<6.5 \times 10^{-12}$ |
| CM5 | Anti-hFcγ | LC5002-005 | hIL-13Rα1:hFc | $1.73 \times 10^5$ | $3.12 \times 10^{-6}$ | $1.8 \times 10^{-11}$ |
| CM5 | Anti-hFcγ | LC5002-007 | hIL-13Rα1:hFc | $1.19 \times 10^5$ | $1 \times 10^{-6}$ | $<8.4 \times 10^{-12}$ | b) Affinity Analysis of HuMabs LC5002-003, -005 and -007 using the Extracellular Domain of hIL-13Rα1 Cleaved from of hIL-13Rα1:hFc Chimeric Protein For interaction analysis, a Biacore 3000 instrument was used. Running and reaction buffer was HBS-P (10 mM HEPES, 150 mM NaCl, 0.005% polysurfactant P, pH 7.4) at 25° C. Capturing antibody molecules (anti-hFcγ) were amine-coupled at a concentration of 100 μg/ml at a flow rate of 5 μl/min for 20 minutes. HuMabs were injected at concentrations of 10 μg/ml at a flow rate of 10 μl/min for 30 seconds. Cleaved hIL-13Rα1 molecules (Mw 40 kDa) were injected for 200 seconds at seven concentrations between 1.56 nM and 100 nM and washed with HBS-P for five minutes. Regeneration of the surface was accomplished by two injections of 100 mM HCl for 1 min each at a flow rate of 10 μg/ml. The chip, assay format and sequence of injections and kinetic data correspond to the description in the following Table 3. Kinetic data were calculated by fitting kinetic data to a 1:1 Langmuir binding model.

Example 14

Testing the Crossreactivity of HuMab with hIL-13Rα2 and hIL-4Rα by ELISA

Chimeric proteins hIL-13Rα2:hFc and hIL-4Rα:hFc (R&D Systems, UK) were dissolved in PBS (1 μg/ml) and allowed to adsorb to microtiter plates (NUNC Maxisorb) by incubation over night at 4° C. After washing the plates with washing buffer (WB=0.9% NaCl; 0.1% Tween® 20) unspecific binding sites were blocked by addition of 100 μl incubation buffer (IB=PBS with 1% crotein C and 0.1% Tween® 20) and incubation for 30 min at room-temperature (RT). Then serially diluted HuMab and control antibodies (100 μl/well; dilutions in IB) were added and incubated for 1 hour at RT. The plates were again washed and bound antibody was detected by incubation with peroxidase conjugated rabbit anti-human kappa (DAKO, Denmark) in a final dilution of 1:500 in IB. After incubation for 1 h at RT and a subsequent washing step, the plates were developed with ready-to-use ABTS® solution (Roche Diagnostics GmbH, DE) at RT in

TABLE 3

| Chip | Capturing | Ligand | Analyte | $k_a$ (1/Ms) | $k_d$ (1/s) | $K_D$ (M) |
|---|---|---|---|---|---|---|
| C1 | Anti-hFcγ | LC5002-002 | hIL-13Rα1 | $1.1 \times 10^6$ | $6.5 \times 10^{-4}$ | $6.2 \times 10^{-10}$ |
| C1 | Anti-hFcγ | LC5002-003 | hIL-13Rα1 | $1.3 \times 10^6$ | $5.1 \times 10^{-4}$ | $3.9 \times 10^{-10}$ |
| C1 | Anti-hFcγ | LC5002-005 | hIL-13Rα1 | $1.4 \times 10^6$ | $3.0 \times 10^{-4}$ | $2.2 \times 10^{-10}$ |
| C1 | Anti-hFcγ | LC5002-007 | hIL-13Rα1 | $1.9 \times 10^5$ | $8.3 \times 10^{-4}$ | $4.4 \times 10^{-9}$ |
| C1 | Anti-hFcγ | LC5002-005, mutant L234A; L235A | hIL-13Rα1 | $1.4 \times 10^6$ | $2.9 \times 10^{-4}$ | $2.1 \times 10^{-10}$ | c) Comparative Affinity Analysis of Recombinant Variants of LC5002-005 Using the Extracellular Domain of hIL-13Rα1 Cleaved from hIL-13Rα1:hFc Chimeric Protein In these experiments, the affinity of the original IgG1 derived from hybridoma was compared with the affinities of the recombinant variant IgG1-Ala-Ala. For interaction analysis, a Biacore 3000 instrument was used. Running and reaction buffer was HBS-P (10 mM HEPES, 150 mM NaCl, 0.005% polysurfactant P, pH 7.4) at 25° C. Capturing antibody molecules (anti-hFcγ) were amine-coupled at a concentration of 20 μg/ml at a flow rate of 5 μl/min for 20 minutes. HuMabs were injected at concentrations of 10 μg/ml at a flow rate of 10 μl/min for 1 minute. Cleaved hIL-13Rα1 molelcules (analyte) were injected for five minutes at eight concentrations between 1.56 nM and 200 nM and washed with HBS-P for five minutes. Regeneration of the surface was accomplished by two injections of 100 mM HCl for 1 min each. The chip, assay format and sequence of injections and kinetic data correspond to the description in Table 4. Kinetic data were calculated by fitting kinetic data to a bivalent analyte binding model.

the dark. Absorbance was measured at 405 nm after absorbance of the highest concentration reached a sufficient OD.

Figure 4:
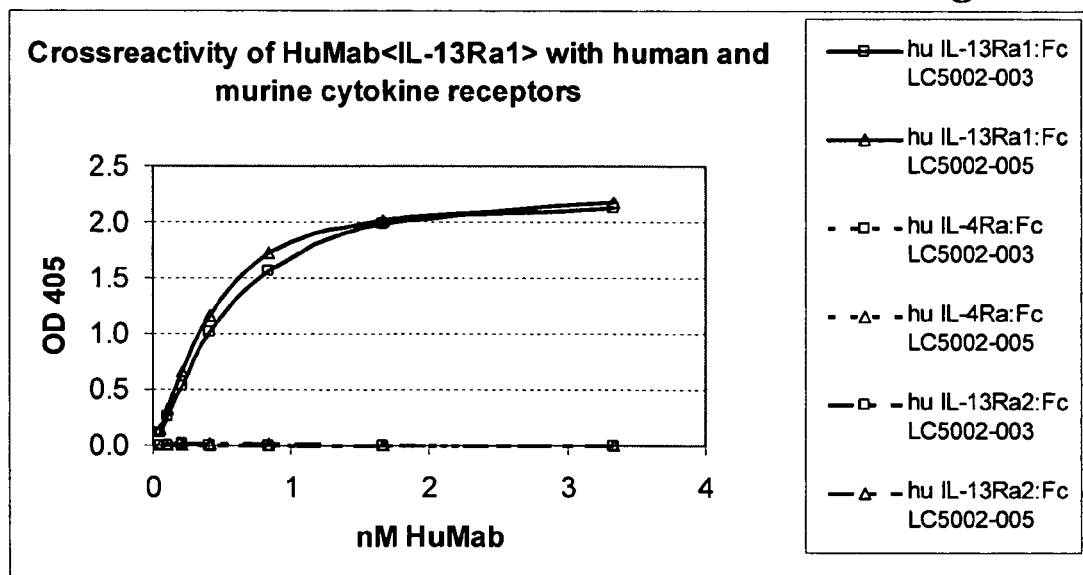
FIG. 4 shows binding of anti-IL-13Rα1 antibodies to hIL-13Rα1 and binding properties to functionally related receptors hIL-13Rα2 and hIL-4Rα.

All antibodies against IL-13Ralpha1 tested were able to bind to immobilized extracelluar domains of human IL-13Rα1, but not neither to hIL-13Rα2 nor to hIL-4Rα (FIG. 4).

Example 15

Crossreactivity of HuMab with Murine IL-13Rα1

Chimeric protein murine IL-13Rα1:hFc (R&D Systems, UK) was dissolved in PBS (1 μg/ml) and allowed to adsorb to microtiter plates (NUNC Maxisorb) by incubation over night at 4° C. After washing the plates with washing buffer (WB=0.9% NaCl; 0.1% Tween® 20), unspecific binding sites were blocked by addition of 100 μl incubation buffer (IB=PBS with 1% Crotein C and 0.1% Tween® 20) and incubation for 30 min at room-temperature (RT). Then, serially diluted HuMab and control antibodies (HuMab anti-KLH and polyclonal goat anti-hIL-13Rα1 (R&D Systems)) were added to the wells (100 μl/well; dilutions in IB) and incubated for 1 hour at RT. The plates were again washed and

TABLE 4

Figure 5:
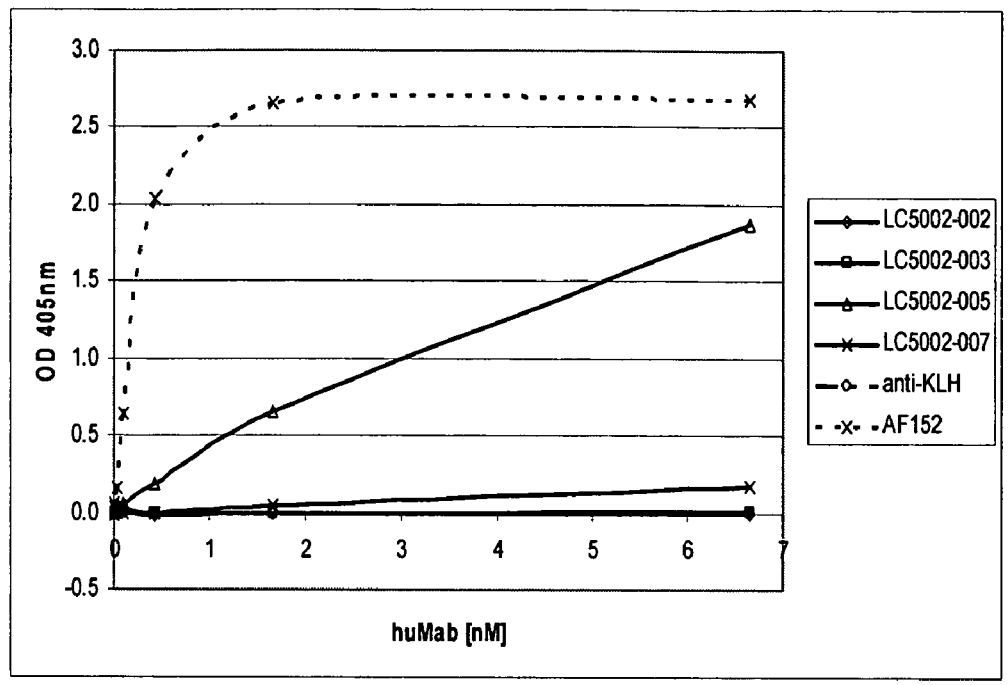
FIG. 5 shows the capacity of anti-IL-13Rα1 antibodies to bind to immobilized recombinant murine IL-13Rα1 polypeptide. Included are polyclonal goat-anti-human IL-13Rα1 antibody AF152 (R&D Systems) and anti-KLH as a negative control HuMab.

| Chip | Capturing | Ligand | Analyte | $k_{a1}$ (1/Ms) | $k_{d1}$ (1/s) | $k_{a2}$ (1/RUs) | $k_{d2}$ (1/s) | $K_D$ (M) |
|---|---|---|---|---|---|---|---|---|
| CM5 | Anti-hFcγ | LC5002-005 | hIL-13Rα1 | $1.33 \times 10^5$ | $3.6 \times 10^{-4}$ | $5.8 \times 10^{-3}$ | 0.06 | $2.7 \times 10^{-9}$ |
| CM5 | Anti-hFcγ | IgG1 ala—ala LC5002-005 | hIL-13Rα1 | $1.53 \times 10^5$ | $4.2 \times 10^{-4}$ | $4.1 \times 10^{-3}$ | 0.04 | $2.8 \times 10^{-9}$ | bound human antibodies were detected by incubation with peroxidase conjugated rabbit anti-human kappa (DAKO, Denmark) in a final dilution of 1:500 in IB. Goat anti-hIL-13Rα1 antibodies bound to the plates were detected by peroxidase-conjugated donkey anti-goat IgG (Santa Cruz; 1:1000 in IB). After incubation for 1 h at RT and a subsequent washing step, the plates were developed with ready-to-use ABTS® solution (Roche Diagnostics GmbH, DE) at RT in the dark. Absorbance was measured at 405 nm after absorbance of the highest concentration reached a sufficient OD (FIG. 5).

Example 16

Crossreactivity of HuMab with Cynomolgus IL-13Rα1

The gene coding for IL-13Rα1 was isolated by RT-PCR from Cynomolgus tissue and transfected into in the murine cell line Ba/F3. In order to test whether the HuMabs crossreact with Cynomolgus IL-13Rα1, the stably transfected Ba/F3 cells as well as the parental Ba/F3 cells were incubated with 10 μg/ml of HuMab and control antibodies. As positive control, a polyclonal goat-anti hIL-13Rα1 (R&D Systems) was used. Negative controls included were: a human IgG1 myeloma protein (Nordic) and normal goat serum. Bound antibodies were detected by FACS analysis using an antibody directed against human IgG conjugated with FITC to detect HuMabs and an antibody directed against goat IgG conjugated with FITC to detect goat antibodies. Mean fluorescence intensities (MFI) were compared for the individual antibodies tested on the transfected Ba/F3 line versus the parental line.

All HuMabs of the invention were able to bind to Cynomolgus IL-13Rα1 expressed in transfected Ba/F3 cells. As expected from the close homology between human and Cynomolgus IL-13Rα1, the polyclonal AF152 antibody also bound to the Cynomolgus IL-13Rα1. The negative control antibodies showed only a marginal increase in MFI when tested with the transfected Ba/F3 cell line (Table 5).

TABLE 5

| | Antibody | MFI Ba/F3 | MFIBa/ F3_Cyno_IL- 13Rα1 | Fold Increase in MFI in the presence of Cyno_IL- 13Rα1 |
|---|---|---|---|---|
| HuMabs | LC5002-002 | 3.9 | 83.7 | 79.8 |
| | LC5002-003 | 3.4 | 82.4 | 79.0 |
| | LC5002-005 | 14.8 | 101.5 | 86.7 |
| | LC5002-007 | 4.1 | 19 | 14.9 |
| Controls | AF152 | 3.2 | 21.2 | 18.0 |
| | Normal goat IgG | 3.3 | 5.7 | 2.4 |
| | Normal human IgG1 (Nordic) | 3.5 | 10.2 | 6.7 |
| | Anti human IgG-FITC only | 3.3 | 5.5 | 2.2 |

Example 17

Binding of IL-13Rα1 HuMabs to Fcγ Receptors (Binding to FcγRIIIa on NK Cells)

To determine the ability of the antibodies of the invention to bind to FcγRIIIa (CD16) on Natural Killer (NK) cells, Peripheral Blood Mononuclear Cells (PBMCs) were isolated and incubated with 20 μg/ml of HuMab antibody and control antibodies in the presence or absence of 20 μg/ml of a blocking mouse antibody to FcγRIIIa (anti-CD16, clone 3G8, RDI, Flanders, N.J.), to verify binding via FcγRIIIa. As negative controls, human IgG2 and IgG4 (The Binding Site), that do not bind FcγRIIIa, were used. Human IgG1 and IgG3 (The Binding Site) were included as positive controls for FcγRIIIa binding. Bound antibodies on NK cells were detected by FACS analysis using a PE-labeled mouse anti-human CD56 (NK-cell surface marker) antibody (BD Biosciences Pharmingen, San Diego, Calif.) in combination with a FITC-labeled goat F(ab)$_2$ anti-human IgG (Fc) antibody (Protos immunoresearch, Burlingame, Calif.). Maximum binding at 20 μg/ml (Bmax: MFI±st.dev) of the HuMab tested was determined.

LC5002-005 was able to bind to FcγRIIIa efficiently (comparable to the control IgG1 antibody) as indicated by a Bmax (MFI) value of 580.6±245.8. Addition of a blocking antibody against FcγRIIIa dramatically reduced binding of LC5002-005 to NK cells (Bmax (MFI) value of 260.4±95.90) indicating specific binding to FcγRIIIa.

LIST OF REFERENCES

Aikawa, M., et al., *Cytokine* 13 (2001) 75-84
Aplin, J. D., and Wriston, J. C. Jr., *CRC Crit. Rev. Biochem.* (1981) 259-306
Ausubel, F., et al., ed. Current Protocols in Molecular Biology, Greene Publishing and Wiley Interscience, New York (1987)
Barnes, L. M., et al., *Cytotechnology* 32 (2000) 109-123
Barnes, L. M., et al., *Biotech. Bioeng.* 73 (2001) 261-270
Berge, S. M., et al., *J. Pharm. Sci.* 66 (1977) 1-19
Boerner, P., et al., *J. Immunol.* 147 (1991) 86-95
Brueggemann M., et al., *J. Exp. Med.* 166 (1987) 1351-1361
Bruggemann, M., et al., *Year Immunol.* 7 (1993) 33-40
Brunhouse, R., and Cebra, J. J., *Mol. Immunol.* 16 (1979) 907-917
Burton, D. R., et al., *Nature* 288 (1980) 338-344
Carter, P., et al., *Proc. Natl. Acad. Sci. USA* 89 (1992) 4285-4289
Chen, J., et al., *International Immunology* 5 (1993) 647-656
Chen, J., et al., *EMBO J.* 12 (1993) 821-830
Choi, T. K., et al., *Nature Genetics* 4 (1993) 117-123
Cole et al., *Monoclonal Antibodies and Cancer Therapy*, Alan R. Liss (1985) p. 77
Durocher, Y., et al., *Nucl. Acids. Res.* 30 (2002) E9
Edelman, G. M., et al., *Proc. Natl. Acad. Sci. USA* 63 (1969) 78-85
Edge, A. S., et al., *Anal. Biochem.* 118 (1981) 131-137
EP 0 307 434
Fishwild, D. M., et al., *Nat. Biotechnol.* 14 (1996) 845-851
Geisse, S., et al., *Protein Expr. Purif.* 8 (1996) 271-282
Graber, P., et al., *Eur. J. Immunol.* 28 (1998) 4286-4298
Harding, F., and Lonberg, N., *Ann. N. Acad. Sci* 764 (1995) 536-546
Hezareh, M., et al., *J. Virol.* 75 (2001) 12161-12168
Hoogenboom, H. R., and Winter, G., *J. Mol. Biol.* 227 (1992) 381-388
Idusogie, E. E., et al., *J. Immunol.* 164 (2000) 4178-4184
Jakobovits, A., et al., *Proc. Natl. Acad. Sci. USA* 90 (1993) 2551-2555
Jakobovits, A., et al., *Nature* 362 (1993) 255-258
Jones, P., et al., *Nature* 321 (1986) 522-525
Kabat, E. A., et al., (1991) Sequences of Proteins of Immunological Interest, Fifth Ed., Public Health Service, National Institutes of Health, Bethesda, Md. (1991), NIH Publication No. 91-3242

Kauftnan, R. J., *Mol. Biotechnol.* 16 (2000) 151-161
Lonberg, N., et al., *Nature* 368 (1994) 856-859
Lonberg, N., *Handbook of Experimental Pharmacology* 113 (1994) 49-101
Lonberg, N., and Huszar, D., *Intern. Rev. Immunol.* 25 (1995) 65-93
Love, T. W., et al., *Methods Enzymol.* 178 (1989) 515-527
Lukas, T. J., et al., *J. Immunol.* 127 (1981) 2555-2560
Makrides, S. C., *Protein Expr. Purif.* 17 (1999) 183-202
Marks, J. D., et al., *J. Mol. Biol.* 222 (1991) 581-597
Meissner, P., et al., *Biotechnol Bioeng* 75 (2001) 197-203
Morgan, A., et al., *Immunology* 86 (1995) 319-324
Morrison, S. L., et al., *Proc. Natl. Acad. Sci. USA* 81 (1984) 6851-6855
Neuberger, M. S., *EMBO J.* 2 (1983) 1373-1378
Norderhaug, L., et al., *J. Immunol. Methods* 204 (1997) 77-87
Obiri, N. I., et al, *J. Biol. Chem.* 270 (1995) 8797-8804
Orlandi, R., et al., *Proc. Natl. Acad. Sci. USA* 86 (1989) 3833-3837
Picard, D., and Schaffner, W., *Nature* 307 (1984) 80-82
Poudrier, J., et al., *J. Immunol.* 30 (2000) 3157-3164
Poudrier J., et al., *J. Immunol.*, 163 (1999) 1153-1161
Queen, C., et al., *Proc. Natl. Acad. Sci. USA* 86 (1989) 10029-10033
Riechmann, L., et al., *Nature* 332 (1988) 323-327
Schlaeger, E.-J., and Christensen, K., *Cytotechnology* 30 (1999) 71-83
Schlaeger, E.-J., *J. Immunol. Methods* 194 (1996) 191-199
Sojahr, H. T., and Bahl, O. P., *Arch. Biochem. Biophys.* 259 (1987) 52-57
SwissProt No. O09030
SwissProt No. P24394
SwissProt No. P35225
SwissProt No. P78552
SwissProt No. Q14627
Taylor, L., et al., *Nucleic Acids Research* 20 (1992) 6287-6295
Taylor, L., et al., *Int. Immunol.* 6 (1994) 579-591
Thommesen, J. E., et al., *Mol. Immunol.* 37 (2000) 995-1004
Thotakura, N. R., and Bahl, O. P., *Meth. Enzymol.* 138 (1987) 350-359
Tuaillon, N., et al., *Proc. Natl. Acad. Sci USA* 90 (1993) 3720-3724
Tuaillon, N., et al., *Immunol.* 152 (1994) 2912-2920
U.S. Pat. No. 4,640,835
U.S. Pat. No. 4,496,689
U.S. Pat. No. 4,301,144
U.S. Pat. No. 4,670,417
U.S. Pat. No. 4,791,192
U.S. Pat. No. 4,179,337
U.S. Pat. No. 5,202,238
U.S. Pat. No. 5,204,244
U.S. Pat. No. 5,545,806
U.S. Pat. No. 5,545,807
U.S. Pat. No. 5,569,825
U.S. Pat. No. 5,625,126
U.S. Pat. No. 5,633,425
U.S. Pat. No. 5,661,016
U.S. Pat. No. 5,770,429
U.S. Pat. No. 5,789,650
U.S. Pat. No. 5,814,318
U.S. Pat. No. 5,874,299
U.S. Pat. No. 5,877,397
van Dijk, M. A., and van de Winkel, J. G., Curr. Opin. Chem. Biol 5 (2001) 368-374
Werner, R. G., *Drug Res.* 48 (1998) 870-880
WO 87/05330
WO 92/22645
WO 92/03918
WO 93/1227
WO 94/25585
WO 96/29417
WO 97/15663
WO 98/24884
WO 01/14424
WO 03/080675

The invention claimed is:

1. An anti-IL-13Rα1 antibody, comprising variable heavy chain amino acid sequences CDR1, CDR2, and CDR3, and variable light chain amino acid sequences CDR1, CDR2 and CDR3, wherein said variable heavy chain CDR1-3 sequences are selected from the group consisting of the variable heavy chain amino acid sequences CDR1-3 of SEQ ID NO: 1, 3, 5 and 9 and wherein said variable light chain CDR1-3 sequences are selected from the group consisting of the variable light chain amino acid sequence CDR1-3 of SEQ ID NO: 2, 4, 6 and 10; or wherein said variable heavy chain CDR1-3 sequences are selected from the variable heavy chain amino acid sequence CDR1-3 of SEQ ID NO:7 and wherein said variable light chain CDR1-3 sequences are selected from the variable light chain amino acid sequence CDR1-3 of SEQ ID NO:8.

2. An antibody according to claim 1, comprising a human γ1-heavy chain comprising
   a) replacement of amino acid sequence $Glu_{233}Leu_{234}Leu_{235}Gly_{236}$(SEQ ID NO: 14) with amino acid sequence $Pro_{233}Val_{234}Ala_{235}$ and/or replacement of amino acid sequence $Ala_{327}Leu_{328}Pro_{329}Ala_{330}Pro_{331}$ (SEQ ID NO: 15) with amino acid sequence $Gly_{327}Leu_{328}Pro_{329}Ser_{330}Ser_{331}$ (SEQ ID NO: 13),
   b) replacement of amino acid sequence $Leu_{234}Leu_{235}$ with amino acid sequence $Ala_{234}Ala_{235}$ or
   c) replacement of amino acids $Asp_{265}$ and $Asn_{297}$ with amino acids $Ala_{265}$ and $Ala_{297}$;
   wherein amino acid residues are numbered according to Kabat.

3. An antibody according to claim 1, wherein said antibody is a human antibody.

4. An antibody according to claim 1, wherein said antibody has an affinity of about $10^{-9}$ M ($K_D$) to about $10^{-13}$ M for binding to IL-13Rα1.

5. An antibody according to claim 1 obtained from hybridoma cell line DSM ACC2709, DSM ACC2710, DSM ACC2711 or DSM ACC2712.

6. An antibody according to claim 1, comprising as heavy chain variable region SEQ ID NO: 1 and as light chain variable region SEQ ID NO: 2, as heavy chain variable region SEQ ID NO: 3 and as light chain variable region of SEQ ID NO: 4, as heavy chain variable region SEQ ID NO: 5 and as light chain variable region SEQ ID NO: 6, as heavy chain variable region SEQ ID NO: 7 and as light chain variable region SEQ ID NO: 8 or as heavy variable region SEQ ID NO: 9 and as light chain variable region SEQ ID NO: 10.

7. An antibody according to claim 1, comprising
   a) as heavy chain variable region SEQ ID NO: 1, as light chain variable region SEQ ID NO: 2, as κ light chain constant region SEQ ID NO: 11 and as γ1 heavy chain constant region SEQ ID NO: 12 optionally with mutations L234A and L235A or D265A and N297A,
   b) as heavy chain variable region SEQ ID NO: 3 and as light chain variable region of SEQ ID NO: 4, as κ light chain constant region SEQ ID NO: 11 and as γ1 heavy chain constant region SEQ ID NO: 12 optionally with mutations L234A and L235A or D265A and N297A,
   c) as heavy chain variable region SEQ ID NO: 5 and as light chain variable region SEQ ID NO: 6, as γ light chain constant region SEQ ID NO: 11 and as γ1 heavy chain constant region SEQ ID NO: 12 optionally with mutations L234A and L235A or D265A and N297A,
   d) as heavy chain variable region SEQ ID NO: 7 and as light chain variable region SEQ ID NO: 8, as κ light chain constant region SEQ ID NO: 11 and as γ1 heavy chain constant region SEQ ID NO: 12 optionally with mutations L234A and L235A or D265A and N297A, or
   e) as heavy variable region SEQ ID NO: 9 and as light chain variable region SEQ ID NO: 10, as κ light chain constant region SEQ ID NO: 11 and as γ1 heavy chain constant region SEQ ID NO: 12 optionally with mutations L234A and L235A or D265A and N2978;
   wherein amino acid residues are numbered according to Kabat.

8. A pharmaceutical composition comprising: an effective amount of an antibody of claim 1; and a pharmaceutically acceptable excipient.

9. Hybridoma cell line DSM ACC2709, DSM ACC2710, DSM ACC2711 or DSM ACC2712.

* * * * *

SEQUENCE LISTING

```
<160> NUMBER OF SEQ ID NOS: 15

<210> SEQ ID NO 1
<211> LENGTH: 119
<212> TYPE: PRT
<213> ORGANISM: Homo sapiens

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Ile Tyr
            20                  25                  30

Ala Met Asn Trp Val Arg Gln Ala Pro Gly Lys Gly Leu Glu Trp Val
        35                  40                  45

Ser Val Ile Ser Gly Arg Gly Ile Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Asp Asp Thr Ala Val Tyr Tyr Cys
                85                  90                  95
```

```
Ala Lys Gly Ser Ser Ser Trp Thr Asp Phe Asp Tyr Trp Gly Gln Gly
            100                 105                 110

Thr Leu Val Thr Val Ser Ser
            115

<210> SEQ ID NO 2
<211> LENGTH: 107
<212> TYPE: PRT
<213> ORGANISM: Homo sapiens

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Arg Trp
            20                  25                  30

Val Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Trp
                85                  90                  95

Thr Phe Gly Gln Gly Thr Lys Val Glu Ile Lys
            100                 105

<210> SEQ ID NO 3
<211> LENGTH: 119
<212> TYPE: PRT
<213> ORGANISM: Homo sapiens

<400> SEQUENCE: 3

Glu Val Gln Leu Leu Glu Ser Gly Gly Asp Leu Ile Gln Pro Gly Gly
1               5                   10                  15

Ser Leu Arg Leu Ser Cys Ala Ala Ser Gly Phe Thr Phe Asn Ile Tyr
            20                  25                  30

Ala Met Asn Trp Val Arg Gln Ala Pro Gly Lys Gly Leu Glu Trp Val
        35                  40                  45

Ser Val Ile Ser Gly Arg Gly Ile Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Val Tyr Tyr Cys
                85                  90                  95

Ala Lys Gly Ser Ser Tyr Trp Thr Asp Phe Asp Tyr Trp Gly Gln Gly
            100                 105                 110

Thr Leu Val Thr Val Ser Ser
            115

<210> SEQ ID NO 4
<211> LENGTH: 107
<212> TYPE: PRT
<213> ORGANISM: Homo sapiens

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
```

```
            20                  25                  30
Leu Ala Trp Tyr Gln Gln Lys Pro Glu Lys Ala Pro Lys Ser Leu Ile
            35                  40                  45

Tyr Ala Ala Ser Ser Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Trp
                85                  90                  95

Thr Phe Gly Gln Gly Thr Lys Val Glu Ile Lys
            100                 105

<210> SEQ ID NO 5
<211> LENGTH: 118
<212> TYPE: PRT
<213> ORGANISM: Homo sapiens

<400> SEQUENCE: 5

Glu Val Gln Val Leu Asp Ser Gly Gly Gly Leu Val Gln Pro Gly Gly
1               5                   10                  15

Ser Leu Arg Leu Ser Cys Thr Ala Ser Gly Phe Thr Phe Arg Leu Tyr
            20                  25                  30

Thr Met Ser Trp Val Arg Gln Thr Pro Gly Arg Gly Leu Glu Trp Val
            35                  40                  45

Ser Gly Ile Ser Gly Ser Gly Leu Ser Thr Tyr Phe Ala Asp Ser Val
            50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Lys Glu Gly Asp Trp Ile Tyr Phe Asp Ser Trp Gly Gln Gly Thr
            100                 105                 110

Leu Val Ile Val Ser Ser
        115

<210> SEQ ID NO 6
<211> LENGTH: 107
<212> TYPE: PRT
<213> ORGANISM: Homo sapiens

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
            35                  40                  45

Tyr Ala Ala Ser Ser Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser His Pro Pro
                85                  90                  95

Thr Phe Gly Gln Gly Thr Lys Leu Glu Ile Lys
            100                 105
```

<210> SEQ ID NO 7
<211> LENGTH: 123
<212> TYPE: PRT
<213> ORGANISM: Homo sapiens

<400> SEQUENCE: 7

Gln Val Gln Leu Val Gln Ser Gly Ala Glu Val Lys Lys Pro Gly Ser
1               5                   10                  15

Ser Val Lys Val Ser Cys Lys Val Ser Gly Gly Thr Phe Ser Ser Tyr
            20                  25                  30

Ala Phe Ser Trp Val Arg Gln Ala Pro Gly Gln Gly Leu Glu Trp Met
        35                  40                  45

Gly Arg Ile Ile Pro Ile Leu Gly Arg Thr Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Val Ser Ser Leu Arg Ser Glu Asp Thr Ala Val Tyr Tyr Cys
                85                  90                  95

Ala Arg Glu Gly Glu Thr Leu Asp Tyr Phe Tyr Tyr Gly Met Asp Val
            100                 105                 110

Trp Gly Gln Gly Thr Thr Val Thr Val Ser Ser
        115                 120

<210> SEQ ID NO 8
<211> LENGTH: 107
<212> TYPE: PRT
<213> ORGANISM: Homo sapiens

<400> SEQUENCE: 8

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Ile Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Gly Ser Ser Leu
                85                  90                  95

Thr Phe Gly Gly Gly Thr Lys Val Glu Ile Lys
            100                 105

<210> SEQ ID NO 9
<211> LENGTH: 119
<212> TYPE: PRT
<213> ORGANISM: Homo sapiens

<400> SEQUENCE: 9

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Ile Tyr
            20                  25                  30

Ala Met Asn Trp Val Arg Gln Ala Pro Gly Lys Gly Leu Glu Trp Val
        35                  40                  45

Ser Val Ile Ser Gly Ser Gly Val Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Gly Ser Ser Trp Tyr Val Asp Phe Asp Tyr Trp Gly Gln Gly
            100                 105                 110

Thr Leu Val Thr Val Ser Ser
            115

<210> SEQ ID NO 10
<211> LENGTH: 107
<212> TYPE: PRT
<213> ORGANISM: Homo sapiens

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Trp
                85                  90                  95

Thr Phe Gly Gln Gly Thr Lys Val Glu Ile Lys
            100                 105

<210> SEQ ID NO 11
<211> LENGTH: 107
<212> TYPE: PRT
<213> ORGANISM: Homo sapiens

<400> SEQUENCE: 11

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 12
<211> LENGTH: 330
<212> TYPE: PRT
<213> ORGANISM: Homo sapiens

<400> SEQUENCE: 12

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 13
<211> LENGTH: 5
<212> TYPE: PRT
<213> ORGANISM: Homo sapiens

<400> SEQUENCE: 13

Gly Leu Pro Ser Ser
1               5

<210> SEQ ID NO 14
<211> LENGTH: 4
<212> TYPE: PRT
<213> ORGANISM: Homo sapiens
```

```
<400> SEQUENCE: 14

Glu Leu Leu Gly
1

<210> SEQ ID NO 15
<211> LENGTH: 5
<212> TYPE: PRT
<213> ORGANISM: Homo sapiens

<400> SEQUENCE: 15

Ala Leu Pro Ala Pro
1               5
```